(12) United States Patent
Nguyen-Kim et al.

(10) Patent No.: US 7,612,160 B2
(45) Date of Patent: Nov. 3, 2009

(54) POLYETHER URETHANE CONTAINING ALLYL GROUPS

(75) Inventors: Son Nguyen-Kim, Hemsbach (DE); Klemens Mathauer, Heidelberg (DE); Claudia Wood, Weinheim (DE)

(73) Assignee: BASF SE, Ludwigshafen (DE)

( * ) Notice: Subject to any disclaimer, the term of this patent is extended or adjusted under 35 U.S.C. 154(b) by 334 days.

(21) Appl. No.: 10/538,760

(22) PCT Filed: Dec. 16, 2003

(86) PCT No.: PCT/EP03/14357

§ 371 (c)(1),
(2), (4) Date: Jun. 10, 2005

(87) PCT Pub. No.: WO2004/055088

PCT Pub. Date: Jul. 1, 2004

(65) Prior Publication Data

US 2006/0247403 A1    Nov. 2, 2006

(30) Foreign Application Priority Data

Dec. 17, 2002    (DE) ................................ 102 59 036

(51) Int. Cl.
*C08G 18/67* (2006.01)
*C08G 18/48* (2006.01)
*C08G 18/61* (2006.01)
*C08L 101/14* (2006.01)
*A61K 8/00* (2006.01)
*A61K 8/30* (2006.01)

(52) U.S. Cl. .............................. 528/75; 528/25; 528/76; 524/591; 524/47; 424/401; 424/70.1; 424/70.11; 424/70.12; 514/937

(58) Field of Classification Search .................. 528/49, 528/75, 76, 33, 25; 524/591, 47; 424/70.1, 424/401, 70.11, 70.12; 514/937

See application file for complete search history.

(56) References Cited

U.S. PATENT DOCUMENTS

| | | | |
|---|---|---|---|
| 3,042,725 A * | 7/1962 | Carter, Jr. | ................... 568/616 |
| 3,714,265 A * | 1/1973 | Bader et al. | ................. 568/606 |
| 4,005,041 A * | 1/1977 | Piggott | ....................... 528/75 |
| 4,246,391 A * | 1/1981 | Watson, Jr. | .................. 528/49 |
| 5,089,586 A | 2/1992 | Piepho et al. | |
| 5,132,329 A * | 7/1992 | Lynch et al. | .................. 521/51 |
| 6,069,217 A | 5/2000 | Nae et al. | |
| 6,524,564 B1 | 2/2003 | Kim et al. | |
| 6,579,517 B1 * | 6/2003 | Kim et al. | ................ 424/70.12 |
| 9,517,131 | 6/2003 | Kim at. | |
| 6,964,774 B1 * | 11/2005 | Dieing et al. | ............... 424/401 |
| 2003/0113285 A1 | 6/2003 | Meffert et al. | |

FOREIGN PATENT DOCUMENTS

WO    WO-00/12588    3/2000

* cited by examiner

*Primary Examiner*—Vasu Jagannathan
*Assistant Examiner*—Benjamin Gillespie
(74) *Attorney, Agent, or Firm*—Connolly Bove Lodge & Hutz LLP

(57) ABSTRACT

The present invention relates to a mono- and/or polyallyl-polyether-urethane, to water-soluble or water-dispersible polymers which comprise such a polyether-urethane in copolymerized form, and to cosmetic or pharmaceutical compositions which comprise a water-soluble or water-dispersible polymer based on a mono- and/or polyallyl-polyether-urethane.

21 Claims, No Drawings

POLYETHER URETHANE CONTAINING ALLYL GROUPS

This application is a National Stage of PCT/EP2003/014357 filed Dec. 16, 2003 which in turn claims priority from German Application 102 59 036.2, filed Dec. 17, 2002.

The present invention relates to a mono- and/or polyallyl-polyether-urethane, to water-soluble or water-dispersible polymers which comprise such a polyether-urethane in copolymerized form, and to cosmetic or pharmaceutical compositions which comprise a water-soluble or water-dispersible polymer based on a mono- and/or polyallyl-polyether-urethane.

Cosmetically and pharmaceutically acceptable water-soluble or water-dispersible polymers are used widely in cosmetics and medicine. They are used, for example, quite generally as thickeners for diverse types of formulations, such as, for examples, gels, creams or emulsions. For these applications, use is often made of branched or crosslinked water-soluble polymers with anionic functionalities, such as, for example, crosslinked polyacrylic acid. For hair cosmetics in particular, crosslinked polymers with film-forming properties are used as conditioners in order to improve the dry and wet combability, the feel to the touch, the shine and/or the appearance of the hair, and also to impart antistatic properties to the hair. As well as the abovementioned carboxylate-containing polymers, the conditioners used are often crosslinked polymers with cationic functionalities which have a high affinity to the surface of the hair, which is negatively charged as a result of its structure. These include, for example, crosslinked copolymers of N-vinylpyrrolidone, quaternized N-vinylimidazole, acrylamide and diallyldimethyl-ammonium chloride (DADMAC).

The provision of products with a complex profile of properties often presents difficulties. For example, a current demand placed on cosmetic and pharmaceutical compositions is to keep the proportion of non-active substances, such as thickeners, as low as possible. There is therefore a need for polymers for cosmetic and pharmaceutical compositions which firstly have good film-forming properties and which are additionally suitable for influencing the rheology of the formulations in the desired manner (so-called self-thickening hair polymers). In addition, esthetic requirements are increasingly placed on cosmetic and pharmaceutical products by the consumer. For example, in the case of such products, a preference for clear, opaque formulations in the form of gels is currently observed. In this connection, however, it has been found that the cosmetically and pharmaceutically acceptable polymers based on low molecular weight crosslinkers known from the prior art are usually in need of improvement with regard to at least one performance property.

For example, they are characterized either by inadequate solubility in water, inadequate film-forming properties or they lack suitability for forming clear gels. There is therefore a need for cosmetically and pharmaceutically compatible, preferably branched or crosslinked, water-soluble polymers which avoid these disadvantages.

WO 99/58100 describes a cosmetic composition comprising at least one crosslinked, water-soluble or water-dispersible polyurethane from at least one polyurethane prepolymer with terminal isocyanate groups and at least one polymer with groups reactive toward isocyanate groups, where at least one of the components comprises a siloxane group.

It is an object of the present invention to provide novel water-soluble or water-dispersible polymer building blocks for the preparation of likewise water-soluble or water-dispersible cosmetically and/or pharmaceutically acceptable polymers. The polymers obtained with these polymer building blocks should preferably have good solubility in water and good film-forming properties and be suitable for the preparation of products in the form of gels.

We have found that this object is achieved by polyether-urethanes which have at least one terminal allyl group on the polymer backbone.

The invention therefore provides a polyether-urethane comprising at least one allyl group which comprises, in incorporated form, a) at least one polyether which comprises a group reactive toward isocyanate groups, and an allyl group,
b) optionally at least one compound which comprises at least two groups reactive toward isocyanate groups, and
c) at least one polyisocyanate.

For the purposes of the present invention, the expression alkyl includes straight-chain and branched alkyl groups. Suitable short-chain alkyl groups are, for example, straight-chain or branched $C_1$-$C_8$-alkyl groups, preferably $C_1$-$C_6$-alkyl groups and particularly preferably $C_1$-$C_4$-alkyl groups. These include, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl etc.

Suitable longer-chain $C_8$-$C_{30}$-alkyl or $C_8$-$C_{30}$-alkenyl groups are straight-chain and branched alkyl or alkenyl groups. Preferably, these are predominantly linear alkyl radicals, as also arise in natural or synthetic fatty acids and fatty alcohols and also oxo alcohols, which may optionally be additionally mono-, di- or polyunsaturated. These include, for example, n-hexyl(ene), n-heptyl(ene), n-octyl(ene), n-nonyl(ene), n-decyl(ene), n-undecyl(ene), n-dodecyl(ene), n-tridecyl(ene), n-tetradecyl(ene), n-pentadecyl(ene), n-hexadecyl(ene), n-heptadecyl(ene), n-octadecyl(ene), n-nonadecyl(ene) etc.

Cycloalkyl is preferably $C_5$-$C_8$-cycloalkyl, such as cyclopentyl, cyclohexyl, cycloheptyl or cyclooctyl.

Aryl includes unsubstituted and substituted aryl groups and is preferably phenyl, tolyl, xylyl, mesityl, naphthyl, fluorenyl, anthracenyl, phenanthrenyl, naphthacenyl and in particular is phenyl, tolyl, xylyl or mesityl.

A suitable embodiment of the polyether-urethanes according to the invention are monoallyl-polyether-urethanes which have an allyl group ($-CH_2-CH=CH_2$) bonded to the polymer backbone via a polyether chain. A further suitable embodiment covers polyallyl-polyether-urethanes which have at least two allyl groups bonded to the polymer backbone via a polyether chain. This is also understood as meaning mixtures of compounds with differing allyl group content, e.g. mixtures which comprise at least one monoallyl-polyether urethane and at least one polyallyl-polyether-urethane.

In the text below, compounds which can be derived from acrylic acid and methacrylic acid are sometimes referred to in shortened form by adding the syllable "(meth)" to the compound derived from acrylic acid.

Polymers based on the polyallyl-polyether-urethanes according to the invention can advantageously be formulated as gels under standard conditions (20° C.). "Gel-like consistency" is shown by compositions which have a higher viscosity than a liquid and which are self-supporting, i.e. they retain shape given to them without a shape-stabilizing coating. In contrast to solid formulations, however, gel-like formulations can be readily deformed under the application of shear forces. The viscosity of the gel-like compositions is preferably in a range of greater than 600 to about 60 000 mPas. The gels are preferably hair gels which have a viscosity of preferably 6000 to 30 000 mPas.

For the purposes of the present invention, water-soluble monomers and polymers are understood as meaning monomers and polymers which dissolve in an amount of at least 1 g/l at 20° C. in water. Hydrophilic monomers are water-soluble or at least water-dispersible. Water-dispersible polymers are understood as meaning polymers which disintegrate into dispersible particles under the application of shear forces, for example by stirring. Crosslinked copolymers based on the polyallyl-polyether-urethanes according to the invention are preferably water-soluble.

The polyallyl-polyether-urethane according to the invention comprises, as component a), at least one polyalkylene glycol monoallyl ether (ether of allyl alcohol with a polyetherdiol). Polyalkylene glycol monoallyl ethers suitable as component a) generally have a number-average molecular weight in the range from about 150 to 10 000, preferably 300 to 5000, particularly preferably 500 to 4000. The polyalkylene glycol radical can be derived, for example, from polyethylene glycols, polypropylene glycols, polytetrahydrofurans and alkylene oxide copolymers. Suitable processes for the preparation of compounds of component a), for example starting from allyl alcohol, allyl halides or allyl glycidyl ether, are known to the person skilled in the art. Such products are commercially available, for example from BASF Aktiengesellschaft under the name Pluriol® A 010R and Pluriol® A 011R. As component a), preference is given to using allyl alcohol alkoxylates which preferably comprise at least one alkylene oxide chosen from ethylene oxide, propylene oxide, epichlorohydrin, 1,2- and 2,3-butylene oxide in copolymerized form. The allyl alcohol alkoxylates can comprise, in copolymerized form, different alkylene oxide units in random distribution or in the form of blocks. Preference is given to allyl alcohol ethoxylates or copolymers which comprise ethylene oxide, in particular copolymers of ethylene oxide and propylene oxide.

Preferably, component a) is chosen from compounds of the formula IV

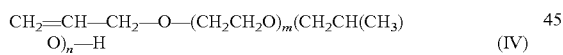

(IV)

in which the order of the alkylene oxide units is arbitrary and m and n are an integer from 0 to 500, where the sum of m and n is >1.

Optionally, the polyallyl-polyether-urethanes according to the invention comprise, in incorporated form, at least one compound b) which is chosen from b1) compounds with a molecular weight in a range from 56 to 280 g/mol which contain two groups reactive toward isocyanate groups per molecule, b2) polyether polyols with a number-average molecular weight in the range from about 300 to 5000, b3) compounds with a number-average molecular weight of more than 280 which contain at least two active hydrogen atoms and at least one siloxane group per molecule, and mixtures thereof.

Suitable compounds b1) are, for example, diols, diamines, aminoalcohols, and mixtures thereof. The molecular weight of these compounds is preferably in a range from about 56 to 280. If desired, up to 3 mol % of said compounds can be replaced by triols or triamines.

Suitable diols b1) are, for example, ethylene glycol, propylene glycol, butylene glycol, neopentyl glycol, cyclohexanedimethylol, di-, tri-, tetra-, penta- or hexaethylene glycol and mixtures thereof. Preference is given to using neopentyl glycol and/or cyclohexanedimethylol.

Suitable aminoalcohols b1) are, for example, 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol etc.

Suitable diamines b1) are, for example, ethylenediamine, propylenediamine, 1,4-diaminobutane, 1,5-diaminopentane and 1,6-diaminohexane.

Component b2) is preferably a polyether polyol with a number-average molecular weight in the range from 400 to 4000, in particular 500 to 3000. Preferred polymers b2) are polyethylene glycols, polypropylene glycols, polytetrahydrofurans etc., block copolymers of ethylene oxide and propylene oxide or block copolymers of ethylene oxide, propylene oxide and butylene oxide which can comprise, in copolymerized form, the alkylene oxide units in random distribution or in the form of blocks. Suitable polytetrahydrofurans b2) can be prepared by cationic polymerization of tetrahydrofuran in the presence of acidic catalysts, such as, for example, sulfuric acid or fluorosulfuric acid. Such preparation processes are known to the person skilled in the art.

The compounds b3) are preferably chosen from polysiloxanes of the formula I.1

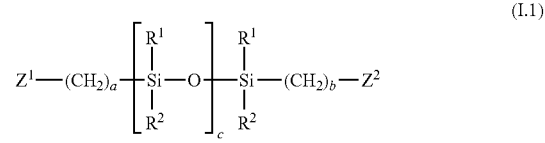

(I.1)

in which a and b, independently of one another, are 1 to 8, c is 2 to 100, $R^1$ and $R^2$, independently of one another, are $C_1$-$C_8$-alkyl, benzyl or phenyl, $Z^1$ and $Z^2$, independently of one another, are OH, $NHR^3$ or a radical of the formula II

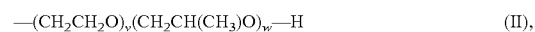

(II), where in the formula II the order of the alkylene oxide units is arbitrary and v and w, independently of one another, are an integer from 0 to 200, where the sum of v and w is >0, $R^3$ is hydrogen, $C_1$-$C_8$-alkyl or $C_5$-$C_8$-cycloalkyl;

polysiloxanes of the formula I.2

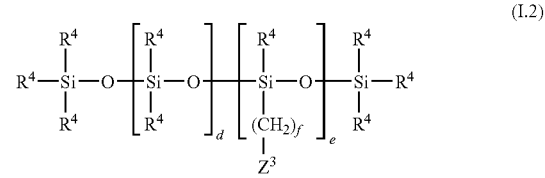

(I.2)

in which
the order of the siloxane units is arbitrary,
the radicals $R^4$ are each, independently of one another, $C_1$-$C_8$-alkyl, preferably methyl, benzyl or phenyl,
d is an integer from 5 to 1000,
e is an integer from 2 to 100,
f is an integer from 2 to 8,
$Z^3$ is OH, $NHR^3$, where $R^3$ is as defined above, or a radical of the formula III

—(OCH$_2$CH$_2$)$_x$(OCH(CH$_3$)CH$_2$)$_y$—OH where in the formula III the order of the alkylene oxide units is arbitrary, x and y, independently of one another, are an integer from 0 to 200, where the sum of x and y is >0, and mixtures thereof.

According to a suitable embodiment, the polysiloxanes b3) of the formula I.1 do not have alkylene oxide radicals of the formula II. These polysiloxanes b3) then preferably have a number-average molecular weight in the range from about 300 to 5000, preferably 400 to 3000.

Suitable polysiloxanes b3) which do not have alkylene oxide radicals are, for example, the Tegomer® products from Goldschmidt.

According to a further suitable embodiment, the polysiloxanes b3) are silicone-poly(alkylene oxide) copolymers of the formula I.1, where at least one or both of the radicals $Z^1$ and/or $Z^2$ are a radical of the formula II.

Preferably, in the formula II, the sum of v and w is chosen such that the molecular weight of the polysiloxanes b3) is in a range from about 300 to 30 000.

Preferably, the total number of the alkylene oxide units of the polysiloxanes b3), i.e. the sum of v and w in the formula II, is in a range from about 3 to 200, preferably 5 to 180.

According to a further suitable embodiment, the polysiloxanes b3) are silicone-poly(alkylene oxide) copolymers of the formula I.2 which have at least two radicals $Z^3$ of the formula III.

Preferably then, in the formula III, the sum of x and y is chosen such that the molecular weight of the polysiloxanes b3) is then in a range from about 300 to 30 000. Preferably, the total number of the alkylene oxide units of the polysiloxanes b3), i.e. the sum of x and y in the formula III, is in a range from about 3 to 200, preferably 5 to 180.

Suitable silicone-poly(alkylene oxide) copolymers b3), which are known, for example, under the international generic name dimethicone, are the Tegopren® products from Goldschmidt, Belsil® 6031 and 6032 from Wacker, Silvet® L from Witco and Pluriol® ST 4005 from BASF Aktiengesellschaft.

Suitable polysiloxanes b3) are also the polydimethylsiloxanes described in EP-A-277 816.

Suitable polyisocyanates c) are chosen from compounds having 2 to 5 isocyanate groups, isocyanate prepolymers with an average number of from 2 to 5 isocyanate groups, and mixtures thereof. These include, for example, aliphatic, cycloaliphatic and aromatic di-, tri- and polyisocyanates. Suitable diisocyanates are, for example, tetramethylene diisocyanate, hexamethylene diisocyanate, 2,3,3-trimethylhexamethylene diisocyanate, 1,4-cyclohexylene diisocyanate, isophorone diisocyanate, 1,4-phenylene diisocyanate, 2,4- and 2,6-tolylene diisocyanate and isomer mixtures thereof (e.g. 80% 2,4-isomer and 20% 2,6-isomer), 1,5-naphthylene diisocyanate, 2,4- and 4,4'-diphenylmethane diisocyanate. A suitable triisocyanate is, for example, triphenylmethane 4,4',4''-triisocyanate. Also suitable are isocyanate prepolymers and polyisocyanates which are obtainable by addition of the abovementioned isocyanates onto polyfunctional hydroxyl or amine group-containing compounds. Also suitable are polyisocyanates which arise as a result of biuret or isocyanurate formation. Preference is given to using aliphatic and/or cycloaliphatic diisocyanates and, in particular, hexamethylene diisocyanate, isophorone diisocyanate and mixtures thereof.

The polyallyl-polyether-urethanes are prepared by reacting the compounds of components a) and, if present, b) with component c). The temperature here is in a range from about 30 to 140° C., preferably about 40 to 100° C. The reaction can take place without solvents or in a suitable inert solvent or solvent mixture. Suitable solvents are aprotic polar solvents, e.g. tetrahydrofuran, ethyl acetate, N-methylpyrrolidone, dimethylformamide and preferably ketones, such as acetone and methyl ethyl ketone. Preferably, the reaction takes place under an inert gas atmosphere, such as, for example, under nitrogen. Furthermore, the reaction preferably takes place at ambient pressure or under increased pressure.

The reaction of the components takes place such that the polyether-urethanes according to the invention have at least one, or for polyallyl-polyether-urethanes at least two, terminal allyl groups. If compounds of component b) are used, it is expedient firstly to prepare an NCO group-containing prepolymer from the compounds a) and c), and, finally, to react this with the compounds b).

Advantageously, it is possible, if the process is carried out appropriately, to dispense with the use of organic and, in particular, organic water-immiscible solvents, or to significantly reduce the amount thereof used during the preparation of the polyether-urethanes according to the invention. This is advantageous since for many cosmetic and pharmaceutical applications the solvents have to be removed prior to formulation of the products.

The invention therefore further provides a process for the preparation of a polyether-urethane comprising at least one allyl group which comprises, in incorporated form,
a) at least one polyether which comprises a group reactive toward isocyanate groups, and an allyl group,
b) optionally at least one compound which comprises at least two groups reactive toward isocyanate groups, and
c) at least one polyisocyanate, and in which
i) in a first stage the compounds a), optionally some of the compounds b) and at least some of the polyisocyanates c) are reacted without the addition of a solvent, at a temperature of at least 60° C. and at a ratio of isocyanate group equivalents to equivalents of groups reactive toward isocyanate groups in a range from 1.5:1 to 2.2:1, to give an isocyanate group-comprising prepolymer, and
ii) in a second stage the prepolymer obtained in step i) is reacted with the compounds b) and c) not already used in step i) to give the polyether-urethane.

Preferably, in stage i), a prepolymer with a glass transition temperature $T_G$ of at most 100° C., preferably of at most 60° C., is obtained.

Preferably, the reaction in step i) takes place at a temperature which is higher than the glass transition temperature of the prepolymer.

In a first embodiment, the compounds b) used in step ii) have hydroxyl groups as groups reactive toward isocyanate groups, and the reaction takes place without the addition of a solvent.

In a second embodiment, the compounds b) used in step ii) have primary or secondary amino groups as groups reactive toward isocyanate groups, and the reaction takes place in the presence of a protic-polar solvent.

The components are preferably used in amounts such that the resulting allyl-polyether-urethane has essentially no free NCO groups. The ratio of NCO equivalents of the compounds of component c) to equivalents of active hydrogen atoms of components a) and, if present, b) is preferably in a range from about 1:1.01 to 1:3, preferably 1:1.1 to 1:2.5, in particular 1:1.2 to 1:2.2. If necessary, any free isocyanate groups still present in the allyl-polyether-urethanes can be deactivated by subsequent reaction with amines, preferably aminoalcohols, or with $C_2$-$C_4$-alcohols, such as ethanol, n-propanol or isopropanol. Suitable amines and aminoalcohols are those mentioned above as component b1), preferably 2-amino-2-methyl-1-propanol.

The allyl-polyether-urethanes according to the invention preferably have 1 to 40, particularly preferably 2 to 25, allyl groups. A particular variant are monoallyl-polyether-urethanes. A further particular variant are polyallyl-polyether-urethanes which have two allyl groups. The abovementioned variants are advantageously suitable for the preparation of water-soluble or water-dispersible copolymers with a low degree of branching or crosslinking. A further particular variant are polyallyl-polyether-urethanes which have 3 to 40, preferably 4 to 25, allyl groups. These are suitable in an advantageous manner for the preparation of water-soluble or water-dispersible copolymers with a somewhat higher degree of branching or crosslinking.

The number-average molecular weight of the allyl-polyether-urethanes is preferably about 300 to 25 000, particularly preferably 400 to 10 000.

Particular preference is given to allyl-polyether-urethanes which comprise, in incorporated form,
a) 40 to 98% by weight, preferably 80 to 96% by weight, of an allyl alcohol ethoxylate with a number-average molecular weight of from 400 to 4000 and
b) 0 to 20% by weight, preferably 1 to 15% by weight, of at least one diol with a molecular weight in the range from 56 to 280 g/mol, and
c) 2 to 40% by weight, preferably 4 to 20% by weight, of at least one diisocyanate, in particular hexamethylene diisocyanate and/or isophorone diisocyanate.

Particular preference is also given to allyl-polyether-urethanes which comprise, in incorporated form,
a) 50 to 90% by weight of an allyl alcohol ethoxylate with a number-average molecular weight of from 400 to 4000
b) 1 to 30% by weight of a polyether polyol with a number-average molecular weight in the range from 300 to 5000 and/or an alkoxylated polydimethylsiloxane with a number-average molecular weight in the range from 3000 to 20 000, and
c) 2 to 49% by weight, preferably 3 to 30% by weight, of at least one diisocyanate, in particular hexamethylene diisocyanate and/or isophorone diisocyanate.

The polyether-urethanes according to the invention are advantageously suitable for the preparation of cosmetically and/or pharmaceutically acceptable water-soluble (or at least water-dispersible) linear, branched or crosslinked polymers. The water-soluble or water-dispersible polymers according to the invention include quite generally the products of free-radical copolymerization of polyether-urethanes according to the invention with compounds which have at least one $\alpha,\beta$-ethylenically unsaturated double bond. Here, the copolymers may be those in which the polyallyl-polyether-urethanes are covalently bonded via one, two or, if present, more than two of their allyl groups. Also covered, however, are copolymers which still have free allyl groups, process products from an at least partial grafting of the $\alpha,\beta$-ethylenically unsaturated compounds onto the polyether chains of the allyl-polyether-urethanes, mixtures of homo- and copolymers of the ethylenically unsaturated compounds with the allyl-polyether-urethanes, and any mixtures of the abovementioned components. Polymers based on the allyl-polyether-urethanes according to the invention have advantageous properties both compared with polymers based on low molecular weight crosslinkers (e.g. diacrylates, methylenebisacrylamide, divinylbenzene, triallylamine, etc.), and also compared with polymers based on high molecular weight crosslinkers having at least two vinyl groups. Thus, compared with conventionally crosslinked polymers, polymers based on polyallyl-polyether-urethanes have improved solubility in water, good rheological (thickening) properties, high flexibility, good film-forming properties and/or the ability to form clear gels.

The invention further provides a water-soluble or water-dispersible polymer which comprises, in copolymerized form, at least one polyallyl-polyether-urethane as defined above, and at least one free-radically polymerizable compound which has at least one $\alpha,\beta$-ethylenically unsaturated double bond.

The water-soluble or water-dispersible polymers according to the invention preferably comprise 1 to 25% by weight, particularly preferably 2 to 20% by weight, based on the total weight of the components used for the polymerization, of at least one polyallyl-polyether-urethane in copolymerized form.

Preferably, in addition to the polyallyl-polyether-urethane, the polymers comprise at least one free-radically polymerizable hydrophilic nonionic compound M1) in copolymerized form.

The water-soluble or water-dispersible polymer according to the invention preferably comprises 50 to 99% by weight, particularly preferably 60 to 98% by weight, in particular 70 to 95% by weight, based on the total weight of the components used for the polymerization, of at least one free-radically polymerizable nonionic compound M1) in copolymerized form.

Preferably, the free-radically polymerizable nonionic compound M1) is chosen from primary amides of $\alpha,\beta$-ethylenically unsaturated monocarboxylic acids, N-vinyllactams, N-vinylamides of saturated monocarboxylic acids, esters of $\alpha,\beta$-ethylenically unsaturated mono- and dicarboxylic acids with $C_2$-$C_4$-alkanediols, esters and amides of $\alpha,\beta$-ethylenically unsaturated mono- and dicarboxylic acids with $C_2$-$C_4$-aminoalcohols which have a primary or secondary amino group, vinyl ethers, nonionic, hydrophilic vinyl- and allyl-substituted heterocyclic compounds and mixtures thereof.

Primary amides of $\alpha,\beta$-ethylenically unsaturated monocarboxylic acids suitable as nonionic monomers M1) are, for example, acrylamide, methacrylamide, ethacrylamide and mixtures thereof. Preference is given to acrylamide and/or methacrylamide.

Preferred hydrophilic nonionic monomers M1) are N-vinyllactams and derivatives thereof which can have, for example, one or more $C_1$-$C_6$-alkyl substituents, such as methyl, ethyl, n-propyl, isopropyl, n-butyl, sec-butyl, tert-butyl etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc. Preference is given to using N-vinylpyrrolidone and/or N-vinylcaprolactam.

N-vinylamides suitable as hydrophilic nonionic monomers M1) are, for example, N-vinylformamide, N-vinyl-N-methylformamide, N-vinylacetamide, N-vinyl-N-methylacetamide, N-vinyl-N-ethyl-acetamide, N-vinylpropionamide, N-vinyl-N-methylpropionamide, N-vinylbutyramide and mixtures thereof. Preference is given to using N-vinylformamide.

Suitable hydrophilic nonionic monomers M1) are also the esters of α,β-ethylenically unsaturated mono- and dicarboxylic acids, such as acrylic acid, methacrylic acid, fumaric acid, maleic acid, itaconic acid, crotonic acid etc., with $C_1$-$C_4$-alkanediols. These include, for example, 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, etc. Preference is given to using hydroxyethyl acrylate and hydroxyethyl methacrylate. Suitable monomers are also the esters of the abovementioned acids with triols and polyols, such as, for example, glycerol, erythritol, pentaerythritol, sorbitol, etc.

Preferably, the water-soluble or water-dispersible polymers comprise, in copolymerized form, at least one hydrophilic nonionic compound M1) chosen from acrylamide, methacrylamide, N-vinylpyrrolidone, N-vinylcaprolactam, N-vinylformamide, N-vinylacetamide and mixtures thereof in copolymerized form.

Preferably, the water-soluble or water-dispersible polymers according to the invention comprise, in addition to at least one polyallyl-polyether-urethane and at least one free-radically polymerizable hydrophilic nonionic compound M1), at least one free-radically polymerizable compound M2) with an α,β-ethylenically unsaturated double bond and at least one ionogenic and/or ionic group per molecule in copolymerized form.

The polymer according to the invention preferably comprises up to 25% by weight, particularly preferably 1 to 20% by weight, in particular 2 to 15% by weight, based on the total weight of the components used for the polymerization, of at least one monomer M2) with at least one ionogenic and/or ionic group per molecule in copolymerized form.

The ionogenic or ionic groups are preferably chosen from carboxylic acid groups, sulfonic acid groups and/or phosphonic acid groups and their salts obtainable by partial or complete neutralization with a base, and also amino groups, which can be partially or completely protonated and quaternized.

Preferably, the monomers M2) with anionogenic/anionic groups are chosen from monoethylenically unsaturated carboxylic acids, sulfonic acids, phosphonic acids and salts and mixtures thereof. These include monoethylenically unsaturated mono- and dicarboxylic acids having 3 to 25, preferably 3 to 6, carbon atoms, which can also be used in the form of their salts or anhydrides. Examples thereof are acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid. These also include the half-esters of monoethylenically unsaturated dicarboxylic acids having 4 to 10, preferably 4 to 6, carbon atoms, e.g. of maleic acid, such as maleic monomethyl ester. These also include monoethylenically unsaturated sulfonic acids and phosphonic acids, for example vinylsulfonic acid, allyl-sulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxy-propylsulfonic acid, styrenesulfonic acid, 2-acrylamido-2-methylpropanesulfonic acid, vinylphosphonic acid and allylphosphonic acid and the salts, in particular the sodium, potassium and ammonium salts, of these acids. The monomers with anionogenic/anionic groups can be used as such or as mixtures with one another. The proportions by weight given all refer to the acid form.

Preferably, for the preparation of the water-soluble or water-dispersible polymers according to the invention, use is made of monomers with anionogenic/anionic groups which are chosen from acrylic acid, methacrylic acid, ethacrylic acid, α-chloroacrylic acid, crotonic acid, maleic acid, maleic anhydride, fumaric acid, itaconic acid, citraconic acid, mesaconic acid, glutaconic acid, aconitic acid and mixtures thereof.

The monomers with anionogenic/anionic groups are particularly preferably chosen from acrylic acid, methacrylic acid and mixtures which comprise acrylic acid and/or methacrylic acid.

According to a further variant, the monomers M2) with ionogenic/ionic groups are those with cationogenic/cationic groups.

The cationogenic and/or cationic groups are preferably nitrogen-containing groups, such as primary, secondary and tertiary amino groups, and also quaternary ammonium groups. The nitrogen-containing groups are preferably tertiary amino groups or quaternary ammonium groups. Charged cationic groups can be produced from the amine nitrogens either by protonation, e.g. with carboxylic acids, such as lactic acid, or mineral acids, such as phosphoric acid, sulfuric acid and hydrochloric acid, or by quaternization, e.g. with alkylating agents, such as $C_1$-$C_4$-alkyl halides or sulfates. Examples of such alkylating agents are ethyl chloride, ethyl bromide, methyl chloride, methyl bromide, dimethyl sulfate and diethyl sulfate.

Suitable monomers are, for example, the esters of α,β-ethylenically unsaturated mono- and dicarboxylic acids with aminoalcohols. Preferred aminoalcohols are $C_2$-$C_{12}$-aminoalcohols which are $C_1$-$C_8$-dialkylated on the amine nitrogen. Suitable as acid component of these esters are, for example, acrylic acid, methacrylic acid, fumaric acid, maleic acid, itaconic acid, crotonic acid, maleic anhydride, monobutyl maleate and mixtures thereof. Preference is given to using acrylic acid, methacrylic acid and mixtures thereof. Preference is given to N,N-dimethylaminomethyl (meth) acrylate, N,N-dimethylaminoethyl (meth)acrylate, N,N-diethylaminoethyl (meth)acrylate, N,N-dimethylaminopropyl (meth) acrylate, N,N-diethylaminopropyl (meth)acrylate and N,N-dimethylaminocyclohexyl (meth)acrylate.

Suitable monomers M2) are also the amides of the abovementioned α,β-ethylenically unsaturated mono- and dicarboxylic acids with diamines which have at least one primary or secondary amino group. Preference is given to diamines which have a tertiary and a primary or secondary amino group. The monomers used are preferably N-[2-(dimethylamino)ethyl]acrylamide, N-[2-(dimethylamino)ethyl]methacrylamide, N-[3-(dimethylamino)propyl]-acrylamide, N-[3-(dimethylamino)propyl]methacrylamide, N-[4-(dimethylamino)butyl]acrylamide, N-[4-(dimethylamino)-butyl]methacrylamide, N-[2-(diethylamino)ethyl]acrylamide, N-[4-(dimethylamino)cyclohexyl]acrylamide, N-[4-(dimethylamino)-cyclohexyl]methacrylamide etc. Particular preference is given to using N-[3-(dimethylamino)propyl]acrylamide and/or N-[3-(dimethylamino)propyl]methacrylamide.

Suitable monomers M2) are also N,N-diallylamines and N,N-diallyl-N-alkylamines and their acid addition salts and quaternization products. Alkyl is here preferably $C_1$-$C_{24}$-alkyl. Preference is given to N,N-diallyl-N-methylamine and N,N-diallyl-N,N-dimethylammonium compounds, such as, for example, the chlorides and bromides.

Suitable monomers M2) with cationogenic/cationic groups are also vinyl- and allyl-substituted nitrogen heterocycles, such as N-vinylimidazole, N-vinyl-2-methylimidazole, vinyl- and allyl-substituted heteroaromatic compounds, such as 2- and 4-vinylpyridine, 2- and 4-allylpyridine, and the salts thereof.

The water-soluble or water-dispersible polymers according to the invention can, if desired, comprise, in copolymerized form, up to 15% by weight, particularly preferably 0.1 to 10% by weight, of at least one further monomer M3). Preferably, these additional monomers are chosen from esters of α,β-ethylenically unsaturated mono- and dicarboxylic acids with $C_1$-$C_{30}$-alkanols, N-alkyl- and N,N-dialkylamides of α,β-ethylenically unsaturated monocarboxylic acids, esters of vinyl alcohol and allyl alcohol with $C_1$-$C_{30}$-monocarboxylic acids, vinylaromatics, vinyl halides, vinylidene halides, $C_1$-$C_8$-monoolefins, nonaromatic hydrocarbons with at least two conjugated double bonds, siloxane macromers and mixtures thereof. Suitable N-alkyl- and N,N-dialkylamides of α,β-ethylenically unsaturated monocarboxylic acids are, for example, N-methyl(meth)acrylamide, N-ethyl(meth)acrylamide, N-propyl(meth)acrylamide, N-tert-butyl(meth)acrylamide, N,N-dimethyl(meth)acrylamide, N,N-diethyl(meth) acrylamide, piperidinyl(meth)acrylamide, morpholinyl (meth)acrylamide, etc.

The water-soluble or water-dispersible polymers according to the invention can, if desired, comprise, in copolymerized form, at least one crosslinker, i.e. a compound with two or more than two ethylenically unsaturated double bonds. Preferably, crosslinkers are used in an amount of from 0.01 to 10% by weight, particularly preferably 0.1 to 3% by weight, based on the total weight of the components for the polymerization of components used.

Crosslinking monomers which can be used are compounds with at least two ethylenically unsaturated double bonds, such as, for example, esters of ethylenically unsaturated carboxylic acids, such as acrylic acid or methacrylic acid and polyhydric alcohols, ethers of at least dihydric alcohols, such as, for example, vinyl ethers or allyl ethers.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis (hydroxymethyl)cyclohexane, hydroxypivalic neopentyl glycol monoester, 2,2-bis(4-hydroxyphenyl)propane, 2,2-bis [4-(2-hydroxypropyl)-phenyl]propane, diethylene glycol, triethylene glycol, tetraethylene glycol, dipropylene glycol, tripropylene glycol, tetrapropylene glycol, 3-thiopentane-1, 5-diol, and also polyethylene glycols, polypropylene glycols and polytetrahydrofurans with molecular weights of in each case 200 to 10 000. Apart from the homopolymers of ethylene oxide or propylene oxide, it is also possible to use block copolymers of ethylene oxide or propylene oxide or copolymers which comprise ethylene oxide and propylene oxide groups in incorporated form. Examples of parent alcohols with more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose, mannose. It is of course also possible to use the polyhydric alcohols following reaction with ethylene oxide or propylene oxide, in the form of the corresponding ethoxylates or propoxylates. The polyhydric alcohols can also firstly be converted into the corresponding glycidyl ethers by reaction with epichlorohydrin.

Further suitable crosslinkers are the vinyl esters or the esters of monohydric, unsaturated alcohols with ethylenically unsaturated $C_3$-$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. It is, however, also possible to esterify the monohydric, unsaturated alcohols with polybasic carboxylic acids, for example malonic acid, tartaric acid, trimellitic acid, phthalic acid, terephthalic acid, citric acid or succinic acid.

Further suitable crosslinkers are esters of unsaturated carboxylic acids with the above-described polyhydric alcohols, for example of oleic acid, crotonic acid, cinnamic acid or 10-undecenoic acid.

Also suitable are straight-chain or branched, linear or cyclic aliphatic or aromatic hydrocarbons which have at least two double bonds, which, in the case of the aliphatic hydrocarbons, must not be conjugated, e.g. divinylbenzene, divinyltoluene, 1,7-octadiene, 1,9-decadiene, 4-vinyl-1-cyclohexene, trivinylcyclohexane or polybutadienes with molecular weights of from 200 to 20 000.

Also suitable are amides of unsaturated carboxylic acids, such as, for example, acrylic acid and methacrylic acid, itaconic acid, maleic acid, and N-allylamines of at least difunctional amines, such as, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dibasic carboxylic acids, as have been described above.

Also suitable are triallylamine or corresponding ammonium salts, e.g. triallylmethylammonium chloride or methyl sulfate, as crosslinkers.

It is also possible to use N-vinyl compounds of urea derivatives, at least difunctional amides, cyanurates or urethanes, for example of urea, ethyleneurea, propyleneurea or tartardiamide, e.g. N,N'-divinylethyleneurea or N,N'-divinylpropyleneurea.

Further suitable crosslinkers are divinyldioxane, tetraallylsilane or tetravinylsilane.

Particularly preferred crosslinkers are, for example, methylenebisacrylamide, divinylbenzene, triallylamine and triallylammonium salts, divinylimidazole, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin, and also allyl or vinyl ethers of polyhydric alcohols, for example 1,2-ethanediol, 1,4-butanediol, diethylene glycol, trimethylolpropane, glycerol, pentaerythritol, sorbitan and sugars, such as sucrose, glucose, mannose.

Particularly preferred crosslinkers are pentaerythritol triallyl ether, allyl ethers of sugars such as sucrose, glucose, mannose, divinylbenzene, N,N'-methylenebisacrylamide, N,N'-divinylethyleneurea, and (meth)acrylic esters of glycol, butanediol, trimethylolpropane or glycerol or (meth)acrylic esters of glycol reacted with ethylene oxide and/or epichlorohydrin, butanediol, trimethylolpropane or glycerol. Very particular preference is given to N,N'-methylenebisacrylamide, diallyltartardiamide, diallyl phthalate, diallylurea, glycol di(meth)acrylate, allyl (meth)acrylate, and polyallyl ethers.

According to a suitable variant, the copolymerization for the preparation of the water-soluble or water-dispersible polymers according to the invention takes place in the presence of at least one compound of component d) which is chosen from d1) polyether-containing compounds,
d2) polymers which have at least 50% by weight of repeat units derived from vinyl alcohol,
d3) starch and starch derivatives, and mixtures thereof.

If the free-radical copolymerization takes place in the presence of at least one compound of component d), copolymers with advantageous properties are obtained. This can be attributed, for example, to the effect of component d) as protective colloid or emulsifier. This can, for example, also result from an at least partial grafting onto component d) as graft base. However, mechanisms other than grafting are also conceivable. The copolymers according to the invention very generally include the process products of free-radical copolymerization, which is understood as meaning, for example, pure graft polymers, mixtures of graft polymers with ungrafted compounds of component d), copolymers of the abovementioned monomers, and any mixtures. Proportions of ungrafted compounds of component d) may be advantageous depending on the intended use of the ampholytic copolymers. Specific compounds d1) can, for example, have an effect as emulsifier or protective colloid.

Preferably, the amount of component d) used is 1 to 25% by weight, particularly preferably 3 to 20% by weight, based on the total weight of the components used for the polymerization.

Suitable polyether-containing compounds d1) are, for example, water-soluble or water-dispersible nonionic polymers which have alkylene oxide repeat units. Preferably, the proportion of alkylene oxide repeat units is at least 30% by weight, based on the total weight of the compound d1). Suitable polyether-containing compounds d1) are, for example, polyalkylene glycols, polyesters based on polyalkylene glycols, polyether-urethanes, and silicone derivatives containing polyalkylene oxide groups.

Polyalkylene glycols suitable as component d1) generally have a number-average molecular weight in the range from about 150 to 100 000, preferably 300 to 50 000, particularly preferably 500 to 40 000. Suitable polyalkylene glycols are, for example, polyethylene glycols, polypropylene glycols, polytetrahydrofurans and alkylene oxide copolymers. Suitable alkylene oxides for the preparation of alkylene oxide copolymers are, for example, ethylene oxide, propylene oxide, epichlorohydrin, 1,2- and 2,3-butylene oxide. The alkylene oxide copolymers can comprise, in copolymerized form, the alkylene oxide units in random distribution or in the form of blocks. Advantageously, homopolymers of ethylene oxide or copolymers which comprise ethylene oxide are used. Preferably, the proportion of repeat units derived from ethylene oxide is 40 to 99% by weight. For example, copolymers of ethylene oxide and propylene oxide, copolymers of ethylene oxide and butylene oxide, and also copolymers of ethylene oxide, propylene oxide and at least one butylene oxide are suitable. Also suitable as component d1) are the allyl ethers of the abovementioned polyalkylene glycols.

Branched polyether-containing polymers d1) can be prepared by, for example, adding at least one of the abovementioned alkylene oxides onto polyalcohol radicals, e.g. onto pentaerythritol, glycerol or onto sugar alcohols, such as D-sorbitol and D-mannitol, or onto polysaccharides, such as cellulose and starch. The alkylene oxide units can be present in the addition product in random distribution or in the form of blocks.

It is also possible to use polyesters of polyalkylene oxides and aliphatic or aromatic dicarboxylic acids, e.g. oxalic acid, succinic acid, adipic acid and terephthalic acid, as polyether-containing compound d1). Suitable polyesters of polyalkylene oxides with molar masses of from 1500 to 25 000 are described, for example, in EP-A-0 743 962. Furthermore, it is also possible to use polycarbonates from the reaction of polyalkylene oxides with phosgene or with carbonates, such as, for example, diphenyl carbonate, and also polyurethanes from the reaction of polyalkylene oxides with aliphatic and aromatic diisocyanates as compound d1).

According to a preferred embodiment, a component d1) which includes at least one polyether-urethane is used for the preparation of the ampholytic copolymers.

Suitable polyether-urethanes are the condensation products of polyether polyols, such as polyetherdiols, with polyisocyanates, such as diisocyanates. Suitable polyether polyols are the abovementioned polyalkylene glycols which are obtainable, for example, from the polymerization of cyclic ethers, such as tetrahydrofuran, or from the reaction of one or more alkylene oxides with a starter molecule which has two or more active hydrogen atoms.

Suitable polyisocyanates are chosen from compounds with 2 to 5 isocyanate groups, isocyanate prepolymers with an average number of from 2 to 5 isocyanate groups, and mixtures thereof. These include, for example, aliphatic, cycloaliphatic and aromatic di-, tri- and polyisocyanates. Suitable diisocyanates are, for example, tetramethylene diisocyanate, hexamethylene diisocyanate, 2,3,3-trimethylhexamethylene diisocyanate, 1,4-cyclohexylene diisocyanate, isophorone diisocyanate, 1,4-phenylene diisocyanate, 2,4- and 2,6-tolylene diisocyanate and isomer mixtures thereof (e.g. 80% 2,4- and 20% 2,6-isomer), 1,5-naphthylene diisocyanate, 2,4- and 4,4'-diphenylmethane diisocyanate. A suitable triisocyanate is, for example, triphenylmethane 4,4', 4"-triisocyanate. Also suitable are isocyanate prepolymers and polyisocyanates which are obtainable by addition of the abovementioned isocyanates onto polyfunctional hydroxyl or amine group-containing compounds. Also suitable are polyisocyanates which arise as a result of biuret or isocyanurate formation. Preference is given to using hexamethylene diisocyanate, trimerized hexamethylene diisocyanate, isophorone diisocyanate, 2,4-tolylene diisocyanate, 2,6-tolylene diisocyanate, and mixtures thereof.

According to a further preferred embodiment, a component d1) which includes at least one polyalkylene oxide-containing silicone derivative is used for the preparation of the ampholytic copolymers.

Suitable silicone derivatives d1) are the compounds known under the INCI names Dimethicone copolyols or silicone surfactants, such as, for example, the compounds obtainable under the trade names Abil® (T. Goldschmidt), Alkasil® (Rhône-Poulenc), Silicone Polyol Copolymer® (Genesee), Belsil® (Wacker), Silwet® (OSI) or Dow Corning (Dow Corning). These include compounds with the CAS numbers 64365-23-7; 68937-54-2; 68938-54-5; 68937-55-3.

Particularly suitable compounds d1) are those which comprise the following structural elements:

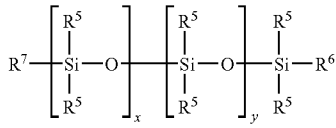 (1)

where:

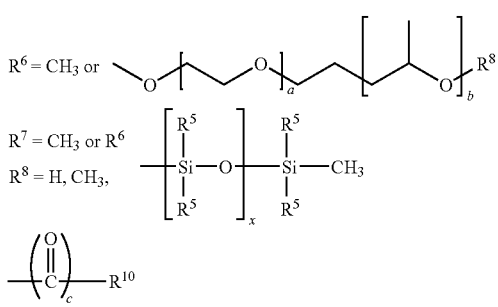

$R^{10}$ is an organic radical of 1 to 40 carbon atoms which can contain amino, carboxylic acid or sulfonate groups or, when c=0 is also the anion of an inorganic acid, and where the radicals $R^5$ may be identical or different, and either originate from the group of aliphatic hydrocarbons having 1 to 20 carbon atoms, are cyclic aliphatic hydrocarbons having 3 to 20 carbon atoms, are of an aromatic nature or are identical to $R^9$, where:

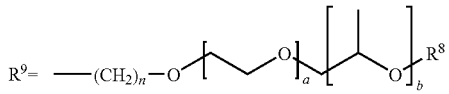

and n is an integer from 1 to 6, x and y are integers such that the molecular weight of the polysiloxane block is between 300 and 30 000, a,b may be integers between 0 and 50, with the proviso that the sum of a and b is greater than 0, and c is 0 or 1.

Preferred radicals $R^6$ and $R^9$ are those in which the sum of a+b is between 5 and 30.

Preferably, the groups $R^5$ are chosen from the following group: methyl, ethyl, propyl, butyl, isobutyl, pentyl, isopentyl, hexyl, octyl, decyl, dodecyl and octadecyl, cycloaliphatic radicals, specifically cyclohexyl, aromatic groups, specifically phenyl or naphthyl, mixed aromatic-aliphatic radicals, such as benzyl or phenylethyl, and also tolyl and xylyl and $R^9$.

Particularly suitable radicals $R^8$ are those in which, when $R^8$=—(CO)$_c$—$R^{10}$, $R^{10}$ is any alkyl, cycloalkyl or aryl radical which has between 1 and 40 carbon atoms and which can carry further ionogenic groups such as $NH_2$, COOH, $SO_3H$.

Preferred inorganic radicals $R^{10}$ are, when c=0, phosphate and sulfate.

Particularly preferred silicone derivatives d) are those of the structure:

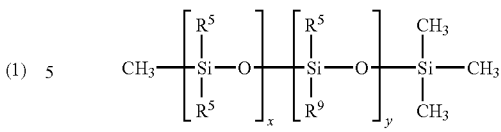

Suitable as graft base are preferably also polymers d2) which have at least 50% by weight of vinyl alcohol units. Preferably, these polymers comprise at least 70% by weight, very particularly preferably 80% by weight, of polyvinyl alcohol units. Such polymers are usually prepared by polymerization of a vinyl ester and subsequent at least partial alcoholysis, aminolysis or hydrolysis. Preference is given to vinyl esters of linear and branched $C_1$-$C_{12}$-carboxylic acids, and very particular preference is given to vinyl acetate. The vinyl esters can of course also be used in a mixture.

Suitable comonomers of the vinyl ester for the synthesis of the graft base d2) are, for example, N-vinylcaprolactam, N-vinylpyrrolidone, N-vinylimidazole, N-vinyl-2-methylimidazole, N-vinyl-4-methylimidazole, 3-methyl-1-vinylimidazolium chloride, 3-methyl-1-vinylimidazolium methyl sulfate, diallylammonium chloride, styrene, alkylstyrenes.

Further suitable comonomers for the preparation of the graft base d2) are, for example, monoethylenically unsaturated $C_3$-$C_6$-carboxylic acids, such as, for example, acrylic acid, methacrylic acid, crotonic acid, fumaric acid, and esters, amides and nitriles thereof, such as, for example, methyl acrylate, ethyl acrylate, methyl methacrylate, ethyl methacrylate, stearyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacrylate, monomethyl maleate, dimethyl maleate, monoethyl maleate, diethyl maleate, 2-ethylhexyl acrylate, 2-ethylhexyl methacrylate, maleic anhydride and its half-ester, alkylene glycol (meth)acrylates, acrylamide, methacrylamide, N-dimethylacrylamide, N-tert-butylacrylamide, acrylonitrile, methacrylonitrile, vinyl ethers, such as, for example, methyl, ethyl, butyl or dodecyl vinyl ether, cationic monomers, such as dialkylaminoalkyl (meth)acrylates and dialkylaminoalkyl(meth)-acrylamides, such as dimethylaminoethyl acrylate, diethylaminoethyl acrylate, diethylaminoethyl methacrylate, and the salts of the last-mentioned monomers with carboxylic acids or mineral acids, and also the quaternized products.

Preferred graft bases d2) are polymers which are prepared by homopolymerization of vinyl acetate and subsequent at least partial hydrolysis, alcoholysis or aminolysis.

Particularly preferred graft bases d2) are polymers which are prepared by homopolymerization of vinyl acetate and subsequent at least partial saponification. Polymers comprising such polyvinyl alcohol units are obtainable under the name Mowiol®.

As component d), preference is given to using starch and/or starch derivatives d3). These include substances which comprise saccharide structures. Such natural substances are, for example, saccharides of vegetable or animal origin or products which are formed by metabolization by microorganisms, and degradation products thereof. Suitable graft bases d3) are, for example, oligosaccharides, polysaccharides, oxidatively, enzymatically or hydrolytically degraded polysaccharides, oxidatively hydrolytically degraded or oxidatively enzymatically degraded polysaccharides, chemically modified oligo- or polysaccharides and mixtures thereof. Preferred products are the compounds specified in U.S. Pat. No. 5,334,287 in column 4, line 20 to column 5, line 45.

Suitable commercially available products are the C-Pur® and C-Dry® products from Cerestar.

If desired, mixtures of compounds of component d) can be used.

A preferred variant are copolymers which are obtainable by copolymerization in the presence of at least one compound d1) which is chosen from polyalkylene oxides, polyalkylene oxide-containing silicone derivatives and mixtures thereof.

Preferably, the copolymers according to the invention have a K value (measured in accordance with E. Fikentscher, Cellulose-Chemie 13 (1932), pp. 58-64) on a 1% strength by weight solution in water in the range from about 30 to 300, particularly preferably 40 to 150.

Depending on the K value, the polymers according to the invention are suitable for a large number of cosmetic and pharmaceutical applications. For example, polymers with a K value up to about 50 can advantageously be formulated as sprays (aerosol sprays and pump sprays). Polymers with a K value in a range from about 50 to 90 are advantageously suitable for gels and foams. For shampoos and skin cosmetic applications, polymers with a K value of at least 80 are preferably suitable.

Preferred polymers are obtainable by free-radical polymerization of 1 to 25% by weight, based on the total weight of the components used for the polymerization, of at least one polyallyl-polyether-urethane, 50 to 99% by weight of at least one free-radically polymerizable nonionic compound M1), 0 to 25% by weight of at least one monomer M2) with at least one ionogenic and/or ionic group per molecule, 0 to 10% by weight of at least one crosslinker, optionally in the presence of up to 25% by weight of at least one component d), as defined above.

The copolymers A) are prepared in accordance with customary processes known to the person skilled in the art, preferably by solution polymerization and precipitation polymerization.

Preferred solvents for solution polymerization are aqueous solvents, such as water and mixtures of water with water-miscible solvents, for example alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of dihydric alcohols, diethylene glycol, triethylene glycol, glycerol and dioxane. Particular preference is given to polymerization in water or a water/alcohol mixture, for example a water/ethanol mixture. The ratio of alcohol to water in such mixtures is preferably in a range from 1:1 to 1:7% by volume. The precipitation polymerization takes place, for example, in an ester, such as ethyl acetate or butyl acetate as solvent. The resulting polymer particles precipitate out of the reaction solution and can be isolated by customary methods, such as filtration by means of subatmospheric pressure. In the case of precipitation polymerization, the polymers obtained usually have higher molecular weights than in the case of solution polymerization.

The polymerization temperatures are preferably in a range from about 30 to 120° C., particularly preferably 40 to 100° C. The polymerization usually takes place under atmospheric pressure, although it can also take place under reduced or increased pressure. A suitable pressure range is between 1 and 5 bar.

To prepare the polymers, the polyallyl-polyether-urethane and the monomers, optionally in the presence of component d), can be polymerized using initiators which form free radicals.

Initiators which can be used for the free-radical polymerization are the peroxo and/or azo compounds customary for this purpose, for example alkali metal or ammonium peroxydisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbamate, bis(o-toloyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, azobis(2-amidinopropane) dihydrochloride or 2-2'-azobis(2-methylbutyronitrile). Also suitable are initiator mixtures or redox initiator systems, such as, for example, ascorbic acid/iron(II) sulfate/sodium peroxodisulfate, tert-butyl hydroperoxide/sodium disulfite, tert-butyl hydroperoxide/sodium hydroxymethanesulfinate, $H_2O_2/Cu^I$.

The amounts of initiator or initiator mixtures used, based on the monomers used, are generally between 0.01 and 10% by weight, preferably between 0.1 and 5% by weight.

To adjust the molecular weight, the polymerization can take place in the presence of at least one regulator. Regulators which can be used are the customary compounds known to the person skilled in the art, such as, for example, sulfur compounds, e.g. mercaptoethanol, 2-ethylhexyl thioglycolate, thioglycolic acid or dodecylmercaptan, and also tribromochloromethane or other compounds which have a regulating effect on the molecular weight of the resulting polymers. A preferred regulator is cysteine.

To achieve the purest possible polymers with a low residual monomer content, the polymerization (main polymerization) can be followed by an afterpolymerization step. The afterpolymerization can take place in the presence of the same initiator system as or a different initiator system to the main polymerization. Preferably, the afterpolymerization takes place at least at the same, preferably at a higher, temperature than the main polymerization. The temperature in the main polymerization and the afterpolymerization is preferably at most 90° C. Preferably, the reaction batch is subjected to a stripping with steam or a steam distillation between the first and the second polymerization step.

If an organic solvent is used in the preparation of the polymers, then this can be removed by customary processes known to the person skilled in the art, e.g. by distillation at reduced pressure.

The polymerization preferably takes place at a pH in the range from 5.5 to 8.0, particularly preferably from 5.6 to 7.5 and especially from 5.8 to 7.3. This generally leads to the attainment of the purest possible polymers with a low residual monomer content, which may be attributed to the fact that amines which are formed as cleavage product and which can in some circumstances react with some monomers to give undesired secondary products under the polymerization conditions are removed. The pH is adjusted by adding a suitable acid, such as lactic acid, tartaric acid, phosphoric acid, or by adding a base, preferably an amine, and in particular an aminoalcohol, such as triethanolamine, methyldiethanolamine, dimethylethanolamine or 2-amino-2-methylpropanol.

Products with particularly high purity and correspondingly advantageous properties for use in cosmetics can be achieved if the reaction product is subjected to a steam distillation or a stripping with steam following the polymerization, optionally before and/or after an afterpolymerization. This treatment with steam also serves, for example, to remove amines and further undesired secondary products which can be removed with steam from the reaction mixture. Preferably, the steam treatment takes place at least between the main polymerization and afterpolymerization. The pH of the polymerization product is preferably adjusted to a value of at most 6.5 prior to the steam treatment. The temperature of the steam used and of the treated polymer solution is preferably at least 90° C.

The polymer solutions can be converted into powder form by various drying processes, such as, for example, spray drying, fluidized spray drying, roller drying or freeze drying. Preference is given to using spray drying. The resulting dry polymer powders can advantageously be converted again into an aqueous solution or dispersion by dissolution or redispersion in water. Pulverulent copolymers have the advantage of better storability, ability to be transported more easily and generally exhibit a lower tendency toward microbial attack.

The invention further provides a cosmetic or pharmaceutical composition comprising
A) at least one water-soluble or water-dispersible polymer as defined above, and
B) at least one cosmetically acceptable carrier.

The cosmetically acceptable carrier B) is preferably chosen from
i) water,
ii) water-miscible organic solvents, preferably $C_1$-$C_4$-alkanols,
iii) oils, fats, waxes,
iv) esters of $C_6$-$C_{30}$-monocarboxylic acids with mono-, di- or trihydric alcohols which are different from iii),
v) saturated acyclic and cyclic hydrocarbons,
vi) fatty acids,
vii) fatty alcohols and mixtures thereof.

The compositions according to the invention have, for example, an oil or fatty component B) which is chosen from: hydrocarbons of low polarity, such as mineral oils; linear saturated hydrocarbons, preferably with more than 8 carbon atoms, such as tetradecane, hexadecane, octadecane etc.; cyclic hydrocarbons, such as decahydronaphthalene; branched hydrocarbons; animal and vegetable oils; waxes; wax esters; vaseline; esters, preferably esters of fatty acids, such as, for example, the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils B) are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150.000 g/mol. Preferred cyclic siloxanes have 4- to 8-membered rings. Suitable cyclic siloxanes are commercially available, for example under the name cyclomethicone.

Preferred oil or fatty components B) are chosen from paraffin and paraffin oils; vaseline; natural fats and oils, such as castor oil, soybean oil, groundnut oil, olive oil, sunflower oil, sesame oil, avocado oil, cocoa butter, almond oil, peach kernel oil, castor oil, cod-liver oil, pork lard, spermaceti, spermaceti oil, sperm oil, wheatgerm oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candililla wax, spermaceti, and mixtures of the abovementioned oil or fatty components.

Suitable cosmetically and pharmaceutically compatible oil or fatty components B) are described in Karl-Heinz Schrader, rundlagen und Rezepturen der Kosmetika [Fundamentals and Formulations of Cosmetics], 2nd edition, Verlag Huthig, Heidelberg, pp. 319-355, to which reference is hereby made.

Suitable hydrophilic carriers B) are chosen from water, mono-, di- or polyhydric alcohols having preferably 1 to 8 carbon atoms, such as ethanol, n-propanol, isopropanol, propylene glycol, glycerol, sorbitol, etc.

The cosmetic compositions according to the invention may be skin cosmetic, dermatological or hair cosmetic compositions.

Preferably, the compositions according to the invention are used in the form of a (low- to high-viscosity) solution, a gel, wax, foam, spray, an ointment, cream, emulsion, suspension, lotion, milk or paste. If desired, liposomes or microspheres can also be used.

The cosmetically or pharmaceutically active compositions according to the invention can additionally comprise cosmetically and/or dermatologically active ingredients and auxiliaries.

Preferably, the cosmetic compositions according to the invention comprise at least one copolymer A as defined above, at least one carrier B as defined above and at least one constituent different to copolymer A which is chosen from cosmetically active ingredients, emulsifiers, surfactants, preservatives, perfume oils, thickeners, hair polymers, hair and skin conditioners, graft polymers, water-soluble or dispersible silicone-containing polymers, light protection agents, bleaches, gel formers, care agents, colorants, tints, tanning agents, dyes, pigments, bodying agents, humectants, refatting agents, collagen, protein hydrolysates, lipids, antioxidants, antifoams, antistats, emollients, softeners.

Suitable cosmetically and/or dermatologically active ingredients are, for example, coloring active ingredients, skin and hair pigmentation agents, tinting agents, tanning agents, bleaches, keratin-hardening substances, antimicrobial active ingredients, light filter active ingredients, repellent active ingredients, substances with hyperemic activity, substances with keratolytic and keratoplastic activity, antidandruff active ingredients, antiphlogistics, substances which have a keratinizing effect, substances which act as antioxidants or as free-radical scavengers, skin moisturizers or humectants, refatting active ingredients, antierythematous or antiallergic active ingredients and mixtures thereof.

Artificially skin-tanning active ingredients which are suitable for tanning the skin without natural or artificial irradiation with UV rays are, for example, dihydroxyacetone, alloxan and walnut shell extract. Suitable keratin-hardening substances are usually active ingredients as are also used in antiperspirants, such as, for example, potassium aluminum sulfate, aluminum hydroxychloride, aluminum lactate, etc. Antimicrobial active ingredients are used in order to destroy microorganisms or to inhibit their growth and thus serve both as preservatives and also as a deodorizing substance which reduces the formation or the intensity of body odor. These include, for example, customary preservatives known to the person skilled in the art, such as p-hydroxybenzoates, imidazolidinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine etc. Suitable light filter active ingredients are substances which absorb UV rays in the UV-B and/or UV-A region. Suitable UV filters are, for example, 2,4,6-triaryl-1,3,5-triazines in which the aryl groups may each carry at least one substituent which is preferably chosen from hydroxyl, alkoxy, specifically methoxy, alkoxycarbonyl, specifically methoxycarbonyl and ethoxycarbonyl and mixtures thereof. Also suitable are p-aminobenzoates, cinnamates, benzophenones, camphor derivatives, and pigments which stop UV rays, such as titanium dioxide, talc and zinc oxide. Suitable repellent active ingredients are compounds which are able to drive away or repel certain animals, in particular insects, from humans. These include, for example, 2-ethyl-1,3-hexanediol, N,N-diethyl-m-toluamide etc. Suitable substances with hyperemic activity which stimulate blood flow through the skin are, for example, ethereal oils, such as dwarf pine, lavender, rosemary, juniper berry, horsechestnut extract, birch leaf extract, hayseed extract, ethyl acetate, camphor, menthol, peppermint oil, rosemary extract, eucalyptus oil, etc. Suitable keratolytic and keratoplastic substances are, for example, salicylic acid, potassium thioglycolate, thioglycolic acid and salts thereof, sulfur, etc. Suitable antidandruff active ingredients are, for example, sulfur, sulfur polyethylene glycol sorbitan monooleate, sulfur ricinol polyethoxylate, zinc pyrithione, aluminum pyrithione, etc. Suitable antiphlogistics which counter skin irritations are, for example, allantoin, bisabolol, Dragosantol, chamomile extract, panthenol, etc.

The cosmetic compositions according to the invention can comprise, as cosmetic and/or pharmaceutical active ingredient (and also optionally as auxiliary), at least one cosmetically or pharmaceutically acceptable polymer different from compounds of component A). Very generally, these include anionic, cationic, amphoteric and neutral polymers. These are preferably water-soluble or at least water-dispersible.

Examples of anionic polymers are homopolymers and copolymers of acrylic acid and methacrylic acid or salts thereof, copolymers of acrylic acid and acrylamide and salts thereof; sodium salts of polyhydroxycarboxylic acids, water-soluble or water-dispersible polyesters, polyurethanes, e.g. Luviset PUR® from BASF, and polyureas. Particularly suitable polymers are copolymers of t-butyl acrylate, ethyl acrylate, methacrylic acid (e.g. Luvimer® 100P), copolymers of ethyl acrylate and methacrylic acid (e.g. Luvimer® MAE), copolymers of N-tert-butylacrylamide, ethyl acrylate, acrylic acid (Ultrahold® 8, strong), copolymers of vinyl acetate, crotonic acid and optionally further vinyl esters (e.g. Luviset® grades), maleic anhydride copolymers, optionally reacted with alcohol, anionic polysiloxanes, e.g. carboxy-functional, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of meth(acrylic acid), $C_4$-$C_{30}$-alkyl vinyl esters, $C_4$-$C_{30}$-alkyl vinyl ethers and hyaluronic acid. Examples of anionic polymers are also vinyl acetate/crotonic acid copolymers, as are available commercially, for example, under the names Resyn® (National Starch) and Gafset® (GAF), and vinylpyrrolidone/vinyl acrylate copolymers, obtainable, for example, under the trade name Luviflex® (BASF). Other suitable polymers are the vinylpyrrolidone/acrylate terpolymer available under the name Luviflex® VBM-35 (BASF), and sodium sulfonate-containing polyamides or sodium sulfonate-containing polyesters.

Further suitable polymers are cationic polymers with the INCI name Polyquaternium, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamido copolymers (Polyquaternium-7) and chitosan. Suitable cationic (quaternized) polymers are also Merquat® (polymer based on dimethyldiallylammonium chloride), Gafquat® (quaternary polymers which are formed by the reaction of polyvinylpyrrolidone with quaternary ammonium compounds), Polymer JR (hydroxyethylcellulose with cationic groups) and vegetable-based cationic polymers, e.g. guar polymers, such as the Jaguar® grades from Rhodia. Also suitable are the polymers with (meth)acrylamide units described in German patent application

P 102 43 573.1.

Further suitable polymers are also neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include, for example, Luviflex® Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF); polyamides, e.g. those based on itaconic acid and aliphatic diamines, as are described, for example, in DE-A-43 33 238.

Suitable polymers are also amphoteric or zwitterionic polymers, such as the octylacrylamide/methyl methacrylate/tert-butylaminoethyl methacrylate/2-hydroxypropyl methacrylate copolymers obtainable under the names Amphomer® (National Starch), and zwitterionic polymers as are disclosed, for example, in the German patent applications DE 39 29 973, DE 21 50 557, DE 28 17 369 and DE 37 08 451. Acrylamidopropyltrimethylammonium chloride/acrylic acid or methacrylic acid copolymers and the alkali metal and ammonium salts thereof are preferred zwitterionic polymers. Other suitable zwitterionic polymers are methacroylethylbetaine/methacrylate copolymers, which are available commercially under the name Amersette® (AMERCHOL), and copolymers of hydroxyethyl methacrylate, methyl methacrylate, N,N-dimethylaminoethyl methacrylate and acrylic acid (Jordapon®).

Suitable polymers are also nonionic, siloxane-containing, water-soluble or -dispersible polymers, e.g. polyether siloxanes, such as Tegopren® (Goldschmidt) or Belsil® (Wacker).

The formulation base of pharmaceutical compositions according to the invention preferably comprises pharmaceutically acceptable auxiliaries. Pharmaceutically acceptable auxiliaries are the auxiliaries which are known for use in the fields of pharmacy, food technology and related fields, in particular the auxiliaries listed in the relevant pharmacopoeia (e.g. DAB Ph. Eur. BP NF), and other auxiliaries whose properties do not preclude a physiological application.

Suitable auxiliaries may be: lubricants, wetting agents, emulsifying and suspending agents, preservatives, antioxidants, antiirritative substances, chelating agents, emulsion stabilizers, film formers, gel formers, odor-masking agents, resins, hydrocolloids, solvents, solubility promoters, neutralizing agents, permeation accelerators, pigments, quaternary ammonium compounds, refatting and superfatting agents, ointment bases, cream bases or oil bases, silicone derivatives, stabilizers, sterilizing agents, propellants, drying agents, opacifiers, thickeners, waxes, softeners, white oils. Formulation in this regard is based on expert knowledge, as given, for example, in Fiedler, H. P. Lexikon der Hilfsstoffe für Pharmazie, Kosmetik und angrenzende Gebiete [Lexicon of auxiliaries for pharmacy, cosmetics and related fields], 4th Ed., Aulendorf: ECV-Editio-Kantor-Verlag, 1996.

To prepare the dermatological compositions according to the invention, the active ingredients can be mixed or diluted with a suitable auxiliary (excipient). Excipients can be solid, semisolid or liquid materials which can serve as vehicles, carriers or medium for the active ingredient. The admixing of further auxiliaries is carried out, where desired, in the manner known to the person skilled in the art.

In a first preferred embodiment, the compositions according to the invention are skin-cleansing compositions.

Preferred skin-cleansing compositions are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, shower and bath preparations, such as washing lotions, shower baths and shower gels, foam baths, oil baths and scrub preparations.

According to a further preferred embodiment, the compositions according to the invention are cosmetic compositions for the care and protection of the skin, nail care compositions or preparations for decorative cosmetics.

Particular preference is given to skincare compositions, personal hygiene compositions, foot care compositions, light protection compositions, repellents, shaving compositions, depilatory compositions, antiacne compositions, make-up, mascara, lipsticks, eye shadows, kohl pencils, eyeliners, blushers and eyebrow pencils.

The skincare compositions according to the invention are, in particular, W/O or O/W skin creams, day creams and night creams, eye creams, face creams, antiwrinkle creams, moisturizing creams, bleaching creams, vitamin creams, skin lotions, care lotions and moisturizing lotions.

Skin cosmetic and dermatological compositions based on the above-described polymers A) exhibit advantageous effects. The polymers can, inter alia, contribute to the moisturizing and conditioning of the skin and to an improvement in the feel of the skin. The polymers can also act as thickeners in the formulations. By adding the polymers according to the invention, it is possible to achieve a considerable improvement in skin compatibility in certain formulations.

Skin cosmetic and dermatological compositions preferably comprise at least one copolymer A) in an amount of from about 0.001 to 30% by weight, preferably 0.01 to 20% by weight, very particularly preferably 0.1 to 12% by weight, based on the total weight of the composition.

Light protection agents based on the copolymers A), in particular, have the property of increasing the residence time of the UV-absorbing ingredients compared with customary auxiliaries such as polyvinylpyrrolidone.

Depending on the field of use, the compositions according to the invention can be applied in a form suitable for skin care, such as, for example, as cream, foam, gel, pencil, mousse, milk, spray (pump spray or spray containing propellant) or lotion.

As well as comprising the polymers A) and suitable carriers, the skin cosmetic preparations can also comprise further active ingredients and auxiliaries customary in skin cosmetics, as described above. These include, preferably, emulsifiers, preservatives, perfume oils, cosmetic active ingredients, such as phytantriol, vitamins A, E and C, retinol, bisabolol, panthenol, light protection agents, bleaches, colorants, tinting agents, tanning agents, collagen, protein hydrolysates, stabilizers, pH regulators, dyes, salts, thickeners, gel formers, bodying agents, silicones, moisturizers, refatting agents and further customary additives.

Preferred oil and fatty components of the skin cosmetic and dermatological compositions are the abovementioned mineral and synthetic oils, such as, for example, paraffins, silicone oils and aliphatic hydrocarbons having more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, vaseline, hydrogenated lanolin and acetylated lanolin, and mixtures thereof.

The polymers according to the invention can also be mixed with traditional polymers where specific properties are to be set.

To set certain properties, such as, for example, improving the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkyl siloxanes, polyaryl siloxanes, polyarylalkyl siloxanes, polyether siloxanes or silicone resins.

The cosmetic or dermatological preparations are prepared by customary methods known to the person skilled in the art.

The cosmetic and dermatological compositions are preferably in the form of emulsions, in particular water-in-oil (W/O) emulsions or oil-in-water (O/W) emulsions. It is, however, also possible to choose other types of formulation, for example hydrodispersions, gels, oils, oleogels, multiple emulsions, for example in the form of W/O/W or O/W/O emulsions, anhydrous ointments or ointment bases, etc.

The emulsions are prepared by known methods. Apart from the copolymer A), the emulsions usually comprise customary constituents, such as fatty alcohols, fatty acid esters and, in particular, fatty acid triglycerides, fatty acids, lanolin and derivatives thereof, natural or synthetic oils or waxes and emulsifiers in the presence of water. The choice of emulsion type-specific additives and the preparation of suitable emulsions is described, for example, in Schrader, Grundlagen und Rezepturen der Kosmetika [Fundamentals and Formulations of Cosmetics], Hüthig Buch Verlag, Heidelberg, 2nd Edition, 1989, third part, to which express reference is made here.

A suitable emulsion, e.g. for a skin cream etc., generally comprises an aqueous phase which is emulsified by means of a suitable emulsifier system in an oil or fatty phase.

The proportion of the emulsifier system in this type of emulsion is preferably about 4 and 35% by weight, based on the total weight of the emulsion. The proportion of the fatty phase is preferably about 20 to 60% by weight. The proportion of the aqueous phase is preferably about 20 and 70%, in each case based on the total weight of the emulsion. The emulsifiers are those customarily used in this type of emulsion. They are chosen, for example, from: $C_{12}$-$C_{18}$-sorbitan fatty acid esters; esters of hydroxystearic acid and $C_{12}$-$C_{30}$-fatty alcohols; mono- and diesters of $C_{12}$-$C_{18}$-fatty acids and glycerol or polyglycerol; condensates of ethylene oxide and propylene glycols; oxypropylenated/oxyethylated $C_{12}$-$C_{18}$-fatty alcohols; polycyclic alcohols, such as sterols; aliphatic alcohols with a high molecular weight, such as lanolin; mixtures of oxypropylenated/polyglycerolated alcohols and magnesium isostearate; succinic esters of polyoxyethylenated or polyoxypropylenated fatty alcohols; and mixtures of magnesium lanolate, calcium lanolate, lithium lanolate, zinc lanolate or aluminum lanolate and hydrogenated lanolin or lanolin alcohol.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil; mineral oils whose distillation start-point under atmospheric pressure is about 250° C. and whose distillation end-point is 410° C., such as, for example, vaseline oil; esters of saturated or unsaturated fatty acids, such as alkyl myristates, e.g. i-propyl, butyl or cetyl myristate, hexadecyl stearate, ethyl or i-propyl palmitate, octanoic or decanoic acid triglycerides and cetyl ricinoleate.

The fatty phase may also comprise silicone oils soluble in other oils, such as dimethylpolysiloxane, methylphenylpolysiloxane and the silicone glycol copolymer, fatty acids and fatty alcohols.

In order to favor the retention of oils, in addition to the polymers A), it is also possible to use waxes, such as, for example, carnauba wax, candililla wax, beeswax, microcrystalline wax, ozokerite wax and the oleates, myristates, linoleates and stearates of Ca, Mg and Al.

The water-in-oil emulsions are generally prepared by introducing the fatty phase and the emulsifier into a reaction vessel. The vessel is heated at a temperature of approximately 50 to 75° C., then the active ingredients and/or auxiliaries which are soluble in oil are added, and water which has been heated beforehand to approximately the same temperature and into which the water-soluble ingredients have optionally been dissolved beforehand is added with stirring. The mixture is stirred until an emulsion of the desired fineness is obtained, which is then left to cool to room temperature, if necessary with a lesser amount of stirring.

According to a further preferred embodiment, the compositions according to the invention are a shower gel, a shampoo formulation or a bath preparation.

Such formulations comprise at least one polymer A) and customary anionic surfactants as base surfactants and amphoteric and/or nonionic surfactants as cosurfactants. Further suitable active ingredients and/or auxiliaries are generally chosen from lipids, perfume oils, dyes, organic acids, preservatives and antioxidants, and thickeners/gel formers, skin conditioning agents and humectants.

These formulations preferably comprise 2 to 50% by weight, preferably 5 to 40% by weight, particularly preferably 8 to 30% by weight, of surfactants, based on the total weight of the formulation.

All anionic, neutral, amphoteric or cationic surfactants customarily used in body-cleansing compositions can be used in the washing, shower and bath preparations.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or amphopropionates, alkyl amphodiacetates or amphodipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also suitable are alkylamine oxides, mono- or dialkylalkanolamides, fatty acid esters of polyethylene glycols, ethoxylated fatty acid amides, alkyl polyglycosides or sorbitan ether esters.

The washing, shower and bath preparations can also comprise customary cationic surfactants such as, for example, quaternary ammonium compounds, for example cetyltrimethylammonium chloride.

In addition, it is also possible to use other customary cationic polymers, such as, for example, copolymers of acrylamide and dimethyldiallylammonium chloride (Polyquaternium-7), cationic cellulose derivatives (Polyquaternium-4, -10), guar hydroxypropyltrimethylammonium chloride (INCI: Hydroxylpropyl Guar Hydroxypropyltrimonium Chloride), copolymers of N-vinylpyrrolidone and quaternized N-vinylimidazole (Polyquaternium-16, -44, -46), copolymers of N-vinylpyrrolidone/dimethylaminoethyl methacrylate, quaternized with diethyl sulfate (Polyquaternium-11) and others.

The shower gel/shampoo formulations can further comprise thickeners, such as, for example, sodium chloride, PEG-55, propylene glycol oleate, PEG-120 methyl glucose dioleate and others, and also preservatives, further active ingredients and auxiliaries and water.

In a further preferred embodiment, the compositions according to the invention are hair-treatment compositions.

Hair-treatment compositions according to the invention preferably comprise at least one copolymer A) in an amount in the range from about 0.1 to 30% by weight, preferably 0.5 to 20% by weight, based on the total weight of the composition.

The hair-treatment compositions according to the invention are preferably in the form of a setting foam, hair tonic, hair mousse, hair gel, shampoo, hairspray or hair foam. Hairsprays include both aerosol sprays and also pump sprays without propellant gas. Hair foams include both aerosol foams and also pump foams without propellant gas.

Preferred hair-treatment compositions are in the form of a gel. Such a hair-treatment composition comprises, for example:

a) 0.1 to 20% by weight, preferably 1 to 10% by weight, of at least one polymer A), as defined above,
b) 0 to 40% by weight of at least one carrier (solvent) which is chosen from $C_2$-$C_5$-alcohols, in particular ethanol,
c) 0.01 to 5% by weight, preferably 0.2 to 3% by weight, of at least one thickener,
d) 0 to 10% by weight, preferably 0.1 to 3% by weight, of at least one setting polymer different from a), preferably a water-soluble, nonionic polymer,
e) 0 to 1% by weight of at least one refatting agent, preferably chosen from glycerol and glycerol derivatives,
f) 0 to 1% by weight of further active ingredients and/or auxiliaries, e.g. at least one silicone compound,
g) 0 to 1% by weight of at least one UV absorber,
h) water ad 100% by weight.

The hair-treatment compositions can also be in the form of lotions (forming water or styling water) hairsprays or hair foams. Hairsprays and hair foams preferably comprise predominantly or exclusively water-soluble or water-dispersible components. If the compounds used in the hairsprays and hair foams according to the invention are water-dispersible, they can be used in the form of aqueous microdispersions with particle diameters of, usually, 1 to 350 nm, preferably 1 to 250 nm. The solids contents of these preparations are customarily in a range from about 0.5 to 20% by weight. These microdispersions generally do not require emulsifiers or surfactants for their stabilization.

Furthermore, the hair-treatment compositions according to the invention can generally comprise customary cosmetic auxiliaries, for example softeners, such as glycerol and glycol; emollients; perfumes; surfactants; UV absorbers; dyes; antistatic agents; agents for improving combability; preservatives; and antifoams.

If the compositions according to the invention are formulated as hairspray, they comprise a sufficient amount of a propellant, for example a low-boiling hydrocarbon or ether, such as propane, butane, isobutane or dimethyl ether. Propellants which can be used are also compressed gases, such as nitrogen, air or carbon dioxide. The amount of propellant here can be kept low in order not to increase the VOC content unnecessarily. This is then generally not more than 55% by weight, based on the total weight of the composition. If desired, however, higher VOC contents of 85% by weight and above are also possible.

The above-described polymers A) can also be used in combination with other hair polymers in the compositions. Suitable polymers are those described above.

The other hair polymers are preferably present in amounts up to 10% by weight, based on the total weight of the composition.

A preferred hair-treatment composition in the form of a hairspray or hair foam comprises:
a) 0.5 to 20% by weight, preferably 1 to 10% by weight, of at least one polymer A), as defined above,
b) 50 to 99.5% by weight, preferably 55 to 99% by weight, of a carrier (solvent), chosen from water and water-miscible solvents, preferably $C_2$-$C_5$-alcohols, in particular ethanol, and mixtures thereof,
c) 3 to 70% by weight, preferably 5 to 50% by weight, of a propellant, preferably chosen from dimethyl ether and alkanes, such as, for example, propane/butane mixtures,
d) 0 to 10% by weight, preferably 0.1 to 10% by weight, of at least one hair polymer different from a), preferably a water-soluble or -dispersible polymer,
e) 0 to 0.5% by weight, preferably 0.001 to 2% by weight, of at least one water-soluble or water-dispersible silicone compound, and optionally further active ingredients and/or auxiliaries, as defined above.

The composition according to the invention can comprise, as component e), at least one nonionic, siloxane-containing, water-soluble or -dispersible polymer, in particular chosen from the above-described polyether siloxanes. The proportion of this component is then generally about 0.001 to 2% by weight, based on the total weight of the composition.

The copolymers A) are suitable in an advantageous manner for adjusting the rheological properties of formulations which comprise them. They act as thickeners, meaning that the use of additional thickening substances can often be dispensed with or the amount of such thickeners used can at least be reduced.

The copolymers A) are suitable in an advantageous manner as auxiliaries in pharmacy, e.g. as tablet coatings, binders or coating of capsules, as or in (a) coating composition(s) for the textile, paper, printing and leather industry, and for agrochemicals.

The present invention further provides a process for the preparation of a copolymer A defined as above by free-radical polymerization of the monomers a) with at least one further monomer chosen from the monomers b) and c) optionally in the presence of up to 25% by weight, based on the total weight of components a) to d), of a water-soluble component d), which comprises carrying out the polymerization in an aqueous solvent. The above statements regarding the preferred embodiments of the polymerization for the preparation of the copolymer A according to the invention apply here correspondingly.

EXAMPLES

1. Preparation of polyallyl-polyether-urethanes

I) Mono-/diallyl-polyether-urethane

Example A

Feed Material 500 g (=1 mol) of Pluriol® A 010R (BASF Aktienges.)

83 g (=0.5 mol) of hexamethylene diisocyanate

In a four-necked flask equipped with stirrer, dropping funnel, thermometer, reflux condenser and a device for working under nitrogen, 500 g (1 mol) of Pluriol® A 010R and 0.1 g of tetrabutyl orthotitanate were dissolved in 150 g of methyl ethyl ketone with heating to a temperature of about 50° C. and with stirring. Then, with stirring, 83 g (0.5 mol) of hexamethylene diisocyanate were added dropwise, during which the reaction temperature increased. Under reflux, the reaction mixture was stirred for about 2 h. The reaction mixture was diluted with 435 g of ethanol and then cooled to room temperature. This gave a clear 50% strength by weight polyallyl-polyether-urethane solution.

The polyallyl-polyether-urethane oligomers B to F were prepared analogously. Furthermore, the allyl-polyether-urethanes L to O (for which solvent-free or low-solvent preparation processes are given below) can also be prepared by this method.

II) Dimethylsiloxane-containing polyallyl-polyether-urethane

Example G

Feed Material 50 g (=0.1 mol) of Pluriol® A 010R (BASF Aktienges.)

22.2 g (=0.1 mol) of isophorone diisocyanate 133 g (=0.038 mol) of Pluriol® ST 4005 (BASF Aktienges.)

In a four-necked flask equipped with stirrer, dropping funnel, thermometer, reflux condenser and a device for working under nitrogen, 50 g (0.1 mol) of Pluriol® A 010R and 0.03 g of tetrabutyl orthotitanate were placed in 15 g of methyl ethyl ketone with heating to a temperature of about 50° C. and with stirring. Then, with stirring, 22.2 g (0.1 mol) of isophorone diisocyanate were added dropwise, during which the reaction temperature increased. After stirring for 20 minutes at 80° C., 133 g (=0.038 mol) of Pluriol® ST 4005 were added. The reaction mixture was stirred for a further 3 h at 80° C., then admixed with 190 g of ethanol and stirred for a further 30 minutes at 80° C. After cooling to room temperature, a clear 50% strength by weight polyallyl-polyether-urethane solution was obtained.

The polyallyl-polyurethanes H to K were prepared analogously.

III) Allyl Group-containing polyether-urethanes

Example L

The preparation took place in the apparatus described in example A without solvent in a single-stage process.

Example M

Two-stage process, stage 1 without solvent, stage 2 in ethanol.

In an apparatus as described in example A, 57% of the total amount of polyethylene glycol used, the Pluriol® A 010R and the isophorone diisocyanate were reacted without a solvent with heating to a temperature of about 80° C. to give an isocyanate group-containing prepolymer. After cooling to about 40° C., ethanol was added and the prepolymer was reacted with the remaining amount of polyethylene glycol, the Tegomer A-Si 2122 and the hexamethylene diisocyanate to give the end product.

Example N

Two-stage preparation process, Pluriol® A 010R and IPDI in the first stage, Pluriol® ST 4005 in the second stage, both stages without solvent.

Example O

Two-stage process, polyethylene glycol, Pluriol® A 010R and IPDI in the first stage, Pluriol® ST 4005 in the second stage, both stages without solvent.

TABLE 1

| | Polyallyl-polyether-urethanes | | | | | | | |
|---|---|---|---|---|---|---|---|---|
| | Pluriol® A 010R [mol %] | Pluriol® A 011R [mol %] | Pluriol® ST 4005 [mol %]* | Tegomer H-Si2111 [mol %] | NPG [mol %] | IPDI [mol %] | HDI [mol %] | t-BAEMA [mol %] |
| A | 66.67 | — | — | — | — | — | 33.33 | — |
| B | 57.14 | — | — | — | 7.14 | — | 35.72 | — |
| C | 62.07 | — | — | 1.72 | 1.72 | — | 34.49 | — |
| D | — | 54.23 | — | 1.70 | — | — | 33.90 | 10.17 |
| E | — | 66.67 | — | — | — | 33.33 | — | — |
| F | 57.14 | — | — | 7.14 | — | 35.72 | — | — |
| G | 42.02 | — | 15.96 | — | — | 42.02 | — | — |
| H | — | 42.02 | 15.96 | — | — | 42.02 | — | — |
| I | 42.02 | — | 15.96 | — | — | 21.01 | 21.01 | — |
| K | — | 38.76 | 14.73 | — | 7.75 | 38.76 | — | — |

Pluriol® A 010R: allyl alcohol ethoxylate, $M_w$ = about 500, BASF Aktienges.
Pluriol® A 011R: allyl alcohol ethoxylate propoxylate, $M_w$ = about 2000, BASF Aktienges.
Pluriol® ST 4005: ethoxylated propoxylated polydimethyl siloxane, $M_w$ = about 8000, BASF Aktienges. *$M_w$ about 3500 (converted for silicone with two OH groups)
Tegomer H-Si 2111: poly(dimethylsiloxane)diol, $M_w$ = about 900, Goldschmidt
NPG: neopentyl glycol
IPDI: isophorone diisocyanate
HDI: hexamethylene diisocyanate
t-BAEMA: tert-butylaminoethyl methacrylate

TABLE 2

Allyl group-containing polyether-urethanes

|   | PEG 1000 [mol %] | Pluriol ® A 010R [mol %] | Tegomer H-Si 2122 [mol %] | Tegomer A-Si 2122 [mol %] | Pluriol ® ST 4005 [mol %] | IPDI [mol %] | HDI [mol %] |
|---|---|---|---|---|---|---|---|
| L | 10 | 40 | 10 | | | 40 | |
| M | 31.82 | 18.18 | | 4.55 | | 31.82 | 13.63 |
| N | | 38.46 | | | 23.08 | 38.46 | |
| O | 21.74 | 17.39 | | | 17.39 | 43.48 | |

PEG 1000: polyethylene glycol, $M_w = 1000$
Tegomer H-Si 2122: poly(dimethylsiloxane)diol, $M_w$ = about 1000
Tegomer A-Si 2122: poly(dimethylsiloxane)diamine, $M_w$ = about 1000

2. Preparation of Copolymers

Solution Polymerization

Example 6

Copolymer of VP/MAM/VI/polyallyl-polyether-urethane A

Feed 1: monomer mixture of:
 342 g of vinylpyrrolidone
 12 g of vinylimidazole
 1400 g of a 15% strength aqueous solution of methacrylamide (=210 g of methacrylamide and 1190 g of water)
 7.2 g of a 50% strength ethanolic polyallyl-polyether-urethane solution
 3.5 g of 85% strength aqueous phosphoric acid (about 3 g of $H_3PO_4$)

Feed 2: Initiator Solution of:
 6 g of Wako V 50 [2,2'-azobis(2-amidinopropane) dihydrochloride] and
 123 g of water Feed 3: Initiator Solution of:
 4 g of Wako V 50 [2,2'-azobis(2-amidinopropane) dihydrochloride] and
 82 g of water 176 g of feed 1 and 12.9 g of feed 2 were initially introduced into a stirred apparatus with reflux condenser, internal thermometer and 4 separate feed devices, and the mixture was heated to about 65° C. with stirring. After polymerization had started, recognizable when the viscosity starts to increase, at 65° C., the remainder of feed 1 was added over the course of 3 h and the remainder of feed 2 was added over 4 h, during which the internal temperature was increased to about 68° C. When the addition was complete, the reaction mixture was stirred for about a further 2 h at 70° C. Feed 3 was then added over the course of 30 minutes at a temperature of 70° C. and the polymer solution was then afterpolymerized for about a further 2 h at a temperature of about 80° C. The polymer solution was treated for 2 h with steam. This gave an approximately 30% strength aqueous microdispersion.

For stabilization, the solution was treated with 100 ppm of Euxyl K100 from Schulke & Mayr (5-chloro-2-methyl-3-(2)-iso-thiazolone/2-methyl-3-(2H)-isothiazolone/benzyl alcohol).

Pulverulent products were obtained by spray drying or freeze drying.

All of the products listed in table 2 below were polymerized analogously to this.

|    | VP [% by wt.] | MAM [% by wt.] | VFA [% by wt.] | VI [% by wt.] | QVI [% by wt.] | DAD-MAC [% by wt.] | PAPEU 1 [% by wt.] | PAPEU 2 [% by wt.] | DA WA [% by wt.] | PEG 6000 [% by wt.] |
|---|---|---|---|---|---|---|---|---|---|---|
| 1 | 70 | — | 25 | — | — | — | 5 | — | — | — |
| 2 | 70 | — | 22 | — | — | — | 5 | 3 | — | — |
| 3 | 70 | 20 | — | — | — | — | 10 | — | — | — |
| 4 | 60 | 30 | — | — | — | — | 5 | 5 | — | — |
| 5 | 60 | 35 | — | — | — | — | — | 5 | — | — |
| 6 | 57 | 35 | — | 2 | — | — | 6 | — | — | — |
| 7 | 57 | 35 | — | 3 | — | — | 5 | — | — | — |
| 8 | 50 | 30 | — | — | 15 | — | 5 | — | — | — |
| 9 | 40 | 40 | — | — | — | 15 | 5 | — | — | — |
| 10 | — | 40 | 40 | — | — | 15 | 5 | — | — | — |
| 11 | 50 | — | 30 | — | — | 15 | 5 | — | — | — |
| 12 | 50 | — | 30 | — | — | 15 | 5 | — | — | — |
| 13 | 40 | — | 30 | — | — | 25 | 5 | — | — | — |
| 14 | 35 | — | 35 | — | — | 20 | 10 | — | — | — |
| 15 | 35 | — | 35 | — | — | 20 | — | — | 9.5 | 0.5 |
| 16 | 35 | — | 35 | — | — | 20 | — | — | 9.7 | 0.3 |
| 17 | 30 | — | 45 | — | — | 20 | — | — | 4.7 | 0.3 |
| 18 | 20 | — | 55 | — | — | 15 | 5 | — | 4.7 | 0.3 |

-continued

| | VP [% by wt.] | MAM [% by wt.] | VFA [% by wt.] | VI [% by wt.] | QVI [% by wt.] | DAD-MAC [% by wt.] | PAPEU 1 [% by wt.] | PAPEU 2 [% by wt.] | DA WA [% by wt.] | PEG 6000 [% by wt.] |
|---|---|---|---|---|---|---|---|---|---|---|
| 19 | — | — | 80 | — | — | 10 | — | 9.5 | 0.5 | — |
| 20 | — | — | 80 | — | — | 10 | — | 4.5 | 0.5 | 5 |

VP = vinylpyrrolidone
MAM = methacrylamide
VFA = vinylformamide
VI = vinylimidazole
QVI = vinylimidazolium methyl chloride
DADMAC = diallyldimethylammonium chloride
PAPEU 1 = polyallyl-polyether-urethane from allyl alcohol ethoxylate
Pluriol ®A 010R, (BASF) and hexamethylene diisocyanate (from example A)
PAPEU 2 = polyallyl-polyether-urethane from allyl alcohol
ethoxylate
Pluriol ®ST 4005, (BASF) and isophorone diisocyanate (from example G)
DAWA = N,N'-diallyltartardiamide
PEG 6000 = polyethylene glycol, $M_n$ = 6000

3. Application Examples

Use in Hair Cosmetics

1) Hair Gels Containing an Anionic Thickener: Example Nos 21-27

| | [%] | CTFA |
|---|---|---|
| Phase 1: | | |
| Polymer 1-7 (30% strength aqueous solution) | 10.0 | |
| Glycerol | 0.3 | |
| Water dist. | 39.2 | |
| Further additives: preservatives, soluble ethoxylated silicone, perfume | q.s. | |
| Phase 2: | | |
| Carbopol 940 (1% strength aqueous suspension) | 30.0 | Carbomer |
| Triethanolamine | 0.5 | |
| Water dist. | 20.0 | |

To prepare hair gels, the components are weighed in and homogenized. Phase 2 forms a clear, solid gel into which phase 1 is slowly stirred.

2) Hair Gels Containing a Further Setting Polymer and Anionic Thickener: Example Nos 28-34

| | [%] | CTFA |
|---|---|---|
| Phase 1: | | |
| Polymer 1-7 (30% strength aqueous solution) | 7.0 | |
| Luviskol VA 64 | 1.0 | Vinylpyrrolidone-vinyl acetate copolymer |
| Uvinul MS 40 | 0.2 | Benzophenone-4 |
| Glycerol | 0.2 | |
| D-Panthenol USP | 0.1 | Panthenol |
| Ethanol | 20.0 | |
| Water dist. | 21.0 | |
| Further additives: preservatives, soluble ethoxylated silicone, perfume | q.s. | |
| Phase 2: | | |
| Carbopol 940 (1% strength aqueous suspension) | 30.0 | Carbomer |
| Triethanolamine | 0.5 | |
| Water dist. | 20.0 | |

Preparation: The components of the two phases are homogenized after being weighed in. Phase 2 forms a clear, solid gel. Phase 1 is slowly stirred into phase 2.

3) Liquid Hair Gels: Example Nos 35-46

| | [%] | CTFA |
|---|---|---|
| Polymer 1-12 (30% strength aqueous solution) | 5.3 | |
| Natrosol 250 L (2% strength aqueous solution) | 25.0 | Hydroxyethyl-cellulose (Hercules) |
| C-Dry MD 1915 (10% strength aqueous solution) | 25.0 | Degraded starch (Cerestar) |
| Water dist. | 44.7 | |
| Further additives: preservatives, soluble ethoxylated silicone, perfume | q.s. | |

Preparation: Weigh in and slowly homogenize at room temperature.

4) Self-thickening Hair Gels (without Additional Thickener): Examples 47-52

| | [%] | CTFA |
|---|---|---|
| Polymer 15-20 (30% strength aqueous solution) | 10.0 | |
| Polymer 6 (30% strength aqueous solution) | 3.3 | |
| Glycerol | 0.2 | |
| Water dist. | 86.5 | |
| Further additives: preservatives, soluble ethoxylated silicone, perfume | q.s. | |

Preparation: The components are weighed in, homogenized at 40° C. and then cooled to room temperature with stirring.

5) Aqueous Hand Pump Gels: Example Nos 53-66

|  | [%] | CTFA |
|---|---|---|
| Polymer 1-14 (30% strength aqueous solution) | 10.0 | |
| Luviskol ® K 90 | 1.0 | Polyvinyl-pyrrolidone (K value 90, BASF) |
| Water dist. | 88.9 | |
| Further additives: preservatives, soluble ethoxylated silicone, perfume | q.s. | |

Preparation: Weigh in and slowly homogenize at room temperature.

6) VOC 10 Hand Pump Spray: Example Nos 67-73

|  | [%] | CTFA |
|---|---|---|
| Polymer 1-7 (30% strength aqueous solution) | 10.0 | |
| Belsil ®DMC 6031 | 0.10 | Ethoxylated silicone (Goldschmidt) |
| Water dist. | 79.89 | |
| Ethanol | 10.0 | |
| Further additives: preservatives, soluble ethoxylated silicone, perfume | q.s. | |

7) VOC 55 Aerosol Hairspray: Example Nos 74-78

|  | [%] | CTFA |
|---|---|---|
| Polymer 1-5 (30% strength aqueous solution) | 3.0 | |
| Luviset ®PUR (30% strength water/ethanol soln.) | 7.0 | (PU dispersion BASF) |
| Water dist. | 35.5 | |
| Dimethyl ether | 30.0 | |
| Ethanol | 24.5 | |
| Further additives: preservatives, soluble ethoxylated silicone, perfume | q.s. | |

Preparation: The polymer components and auxiliaries are weighed in, dissolved in water/ethanol with stirring and then transferred to spray containers. Finally, the propellant gas is added.

8) Setting Foam: Example Nos 79-90

|  | [%] | CTFA |
|---|---|---|
| Polymer 1-12 (30% strength aqueous solution) | 5.0 | |
| Cremophor A 25 (Ceteareth 25/BASF) | 0.2 | |
| Comperlan KD (coamide DEA/Henkel) | 0.1 | |
| Water dist. | 84.6 | |
| Dimethyl ether (3.5 bar, 20° C.) | 10.0 | |
| Further additives: preservatives, soluble ethoxylated silicone, perfume | q.s. | |

Preparation: Weigh in and dissolve with stirring. Transfer to containers and add propellant gas.

9) Wet-look Setting Foam: Examples 91-102

|  | [%] | CTFA |
|---|---|---|
| Polymer 1-12 (30% strength aqueous solution) | 10.0 | |
| Luviquat ® Mono LS | 2.0 | Cocotrimonium methosulfate |
| Glycerol 87% | 5.0 | Glycerol |
| Water dem. | 72.8 | |
| Perfume oil | 0.2 | |
| Propane/butane (3.5 bar, 20° C.) | 10.0 | |
| Preservative | q.s. | |

Preparation: Weigh in and dissolve with stirring. Transfer to containers and add propellant gas.

10) Shampoo: Example Nos 103-108

Conditioner Shampoo:

|  | [%] | CTFA |
|---|---|---|
| A) Texapon NSO 28% strength (sodium lauryl sulfate/Henkel) | 50.0 | |
| Comperlan KD (coamide DEA/Henkel) | 1.0 | |
| Polymer 15-20 (30% strength aqueous solution) | 3.0 | |
| Water dist. | 17.0 | |
| Perfume oil | q.s. | |
| B) Water | 27.5 | |
| Sodium chloride | 1.5 | |
| Preservative | q.s. | |

Preparation: Weigh in and separately dissolve and mix phases A) and B) with stirring. Slowly stir phase B) into phase A).

Use in Skin Cosmetics:

11) Standard O/W Cream: Example Nos 109-120

|  | [%] | CTFA |
|---|---|---|
| Oil phase: | | |
| Cremophor A6 | 3.5 | Ceteareth-6 and stearyl alcohol |
| Cremophor A25 | 3.5 | Ceteareth-25 |
| Glycerol monostearate s.e. | 2.5 | Glyceryl stearate |
| Paraffin oil | 7.5 | Paraffin oil |
| Cetyl alcohol | 2.5 | Cetyl alcohol |
| Luvitol EHO | 3.2 | Cetearyl octanoate |
| Vitamin-E acetate | 1.0 | Tocopheryl acetate |
| Nip-Nip | 0.1 | Methyl and propyl 4-hydroxy-benzoates (7:3) |
| Water phase: | | |
| Polymer 9-20 (30% strength aqueous solution) | 3.0 | |
| Water | 74.6 | |
| 1,2-Propylene glycol | 1.5 | |
| Germall II | 0.1 | Imidazolidinylurea |

Preparation: Weigh in and separately homogenize, with stirring, the oil phase and the water phase at a temperature of 80° C. Slowly stir the water phase into the oil phase. Slowly cool to room temperature with stirring.

12) Day Lotion: Example Nos 121-132

|  | [%] | CTFA |
|---|---|---|
| Oil phase: | | |
| Cremophor A6 | 1.5 | Ceteareth-6 and stearyl alcohol |
| Cremophor A25 | 1.5 | Ceteareth-25 |
| Glycerol monostearate s.e. | 5.0 | Glyceryl stearate |
| Uvinul MS 40 | 0.5 | Benzophenone-4 |
| Paraffin oil | 3.5 | Paraffin oil |
| Cetyl alcohol | 0.5 | Cetyl alcohol |
| Luvitol EHO | 10.0 | Cetearyl octanoate |
| D-Panthenol 50P | 3.0 | Panthenol and propylene glycol |
| Vitamin-E acetate | 1.0 | Tocopheryl acetate |
| Tegiloxan 100 | 0.3 | Dimethicone |
| Nip-Nip | 0.1 | Methyl and propyl 4-hydroxy-benzoates (7:3) |
| Water phase: | | |
| Polymer 9-20 (30% strength aqueous solution) | 1.5 | |
| Water | 70.0 | |
| 1,2-Propylene glycol | 1.5 | |
| Germall II | 0.1 | Imidazolidinylurea |

Preparation: Weigh in and separately homogenize the oil phase and the water phase with stirring at a temperature of 80° C. Slowly stir the water phase into the oil phase. Slowly cool to room temperature with stirring.

We claim:

1. A hair treatment composition comprising water-soluble or water-dispersible polymer which comprises at least one free-radically polymerizable compound which has at least one α,β-ethylenically unsaturated double bond and at least a polyether-urethane in copolymerized form, where the polyether-urethane comprises at least one allyl group, and, in incorporated form,
   a) at least one polyalkylene glycol monoallyl ether having a number-average molecular weight in the range from 300 to 5000,
   b) optionally at least one compound which comprises at least two groups reactive toward isocyanate groups, and
   c) at least one polyisocyanate,
   as setting agent and/or as conditioner.

2. The hair treatment composition as claimed in claim 1, where the composition is in the form of a hair gel, hair mousse, shampoo, setting foam, hair tonic, hair spray or hair foam.

3. A polyether-urethane comprising at least one allyl group, which comprises, in incorporated form,
   a) at least one polyalkylene glycol monoallyl ether having a number-average molecular weight in the range from 300 to 5000,
   b) at least one compound chosen from compounds b3) wherein b3) is at least one compound chosen from: polysiloxanes of the formula I.1

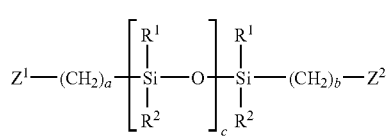

(I.1)

in which
a and b, independently of one another, are 1 to 8,
c is 2 to 100,
$R^1$ and $R^2$, independently of one another, are $C_1$-$C_8$-alkyl, benzyl or phenyl,
$Z^1$ and $R^2$, independently of one another, are OH, $NHR^3$ or a radical of the formula II

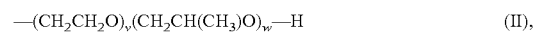   (II), where
in the formula II the alkylene oxide units can be in any order, and
v and w, independently of one another, are an integer from 0 to 200, where the sum of v and w is >0,
$R^3$ is hydrogen, $C_1$-$C_8$-alkyl or $C_5$-$C_8$-cycloalkyl;
polysiloxanes of the formula I.2

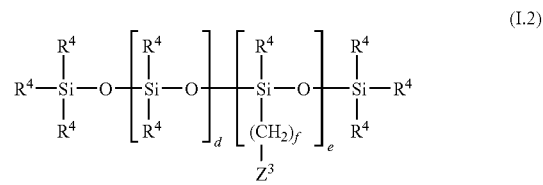

(I.2)

in which
the siloxane units can be in any order,
the radicals $R^4$ are each, independently of one another, $C_1$-$C_8$-alkyl,
d is an integer from 5 to 1000,
e is an integer from 2 to 100,
f is an integer from 2 to 8,
$Z^3$ is OH, $NHR^3$, where $R^3$ is as defined above, or a radical of the formula III

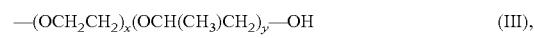   (III), where
in the formula III the alkylene oxide units can be in any order,
x and v independently of one another, are an integer from 0 to 200, where the sum of x and v is >0,
and mixtures thereof,
   c) at least one polyisocyanate.

4. A water-soluble or water-dispersible polymer which comprises, in copolymerized form, at least one polyether-urethane as defined in claim 3, and at least one free-radically polymerizable compound which has at least one α,β-ethylenically unsaturated double bond.

5. A polymer as claimed in claim 4, which comprises, in copolymerized form, at least one free-radically polymerizable hydrophilic nonionic compound M1).

6. A polymer as claimed in claim 5, where the compound M1) is chosen from primary amides of α,β-ethylenically unsaturated monocarboxylic acids, N-vinyllactams, N-vinylamides of saturated monocarboxylic acids, esters of α,β-ethylenically unsaturated mono- and dicarboxylic acids with $C_2$-$C_4$-alkanediols, amides of α,β-ethylenically unsaturated mono- and dicarboxylic acids with $C_2$-$C_4$-aminoalcohols which have a primary or secondary amino group, vinyl ethers, nonionic, hydrophilic vinyl- and allyl-substituted heterocyclic compounds and mixtures thereof.

7. A polymer as claimed in claim 6, which comprises, in copolymerized form, a compound M1) chosen from acrylamide, methacrylamide, N-vinylpyrrolidone, N-vinylcaprolactam, N-vinylformamide, N-vinylacetamide and mixtures thereof.

8. A polymer as claimed in claim 5, which additionally comprises, in copolymerized form, at least one free-radically polymerizable compound M2) with an α,β-ethylenically unsaturated double bond and at least one ionogenic and/or ionic group per molecule.

9. A polymer as claimed in claim 5, which additionally comprises, in copolymerized form, at least one free-radically polymerizable crosslinking compound with at least two α,β-ethylenically unsaturated double bonds per molecule.

10. A polymer as claimed in claim 5, which is obtained by free-radical copolymerization in the presence of a component d) chosen from
   d1) polyether-containing compounds,
   d2) polymers which have at least 50% by weight of repeat units derived from vinyl alcohol,
   d3) starch and starch derivatives,
   and mixtures thereof.

11. A polymer as claimed in claim 5, obtained by free-radical polymerization of
   1 to 25% weight, based on the total weight of the components used for the polymerization, of at least one poly-allyl-polyether-urethane,
   50 to 99% by weight of at least one free-radically polymerizable nonionic compound M1),
   0 to 25% by weight of at least one monomer M2) with at least one ionogenic and/or ionic group per molecule,
   0 to 10% by weight of at least one crosslinker, optionally in the presence of up to 25% by weight of at least one component d), as defined in claim 10.

12. A process for the preparation of a polymer as defined in claim 5 by free-radical polymerization in an aqueous solvent at a pH of from 5.5 to 8.0.

13. A process as claimed in claim 12, comprising a first polymerization step and a subsequent second polymerization step, where the reaction mixture between the first and second polymerization step is subjected to stripping with steam or to a steam distillation.

14. A cosmetic or pharmaceutical composition comprising
   A) at least one water-soluble or water-dispersible polymer as defined in claim 4, and
   B) at least one cosmetically or pharmaceutically acceptable carrier.

15. A composition as claimed in claim 14, where the component B) is chosen from
   i) water,
   ii) water-miscible organic solvents,
   i) oils, fats, waxes,
   ii) esters of $C_6$-$C_{30}$-monocarboxylic acids with mono-, di- or trihydric alcohols which are different from iii),
   iii) saturated acyclic and cyclic hydrocarbons,
   iv) fatty acids,
   v) fatty alcohols
   and mixtures thereof.

16. A composition as claimed in claim 14, further comprising at least on constituent different from copolymer A which is chosen form cosmetically active ingredients, emulsifiers, surfactants, preservatives, perfume oils, thickeners, hair polymers, hair and skin conditioners, graft polymers, water-soluble or dispersible silicone-containing polymers, light protection agents, bleaches, gel formers, care agents, colorants, tints, tanning agents, dyes, pigments, bodying agents, humectants, refatting agents, collagen, protein hydrolysates, lipids, antioxidants, antifoams, antistats, emollients, and softeners.

17. A composition as claimed in claim 14 in the form of a solution, a gel, wax, foam, spray, an ointment, cream, emulsion, suspension, lotion, milk or paste.

18. A cosmetic or pharmaceutical composition comprising a polymer as defined in claim 4 in skin cleansing compositions, compositions for the care and protection of the skin, nail care compositions, preparations for decorative cosmetics and hair treatment compositions.

19. The cosmetic or pharmaceutical composition as claimed in claim 18 in hair treatment compositions as thickener, setting agent and/or as conditioner.

20. The cosmetic or pharmaceutical composition as claimed in claim 19, where the composition is in the form of a hair gel, hair mousse, shampoo, setting foam, hair tonic, hair spray or hair foam.

21. A composition comprising a polymer as defined in claim 4 as auxiliary in pharmacy, or as auxiliary in (a) coating composition(s) for solid medicament forms, or as auxiliary in (a) coating composition(s) for the textile, paper, printing or leather industry, or for agrochemistry.

* * * * *